(12) United States Patent

Rheinheimer et al.

(10) Patent No.: US 7,695,728 B2
(45) Date of Patent: Apr. 13, 2010

(54) 2-SUBSTITUTED PYRIDINES, PROCESSES FOR THEIR PREPARATION AND THEIR USE FOR CONTROLLING HARMFUL FUNGI

(75) Inventors: Joachim Rheinheimer, Ludwigshafen (DE); Frank Schieweck, Heβheim (DE); Thomas Grote, Wachenheim (DE); Carsten Blettner, Hong Kong (CN); Anja Schwögler, Mannheim (DE); Markus Gewehr, Kastellaun (DE); Wassilios Grammenos, Ludwigshafen (DE); Udo Hünger, Mainz (DE); Bernd Müller, Frankenthal (DE); Peter Schäfer, Ottersheim (DE); John-Bryan Speakman, Bobenheim (DE); Maria Scherer, Godramstein (DE); Siegfried Strathmann, Limburgerhof (DE); Ulrich Schöfl, Brühl (DE); Reinhard Stierl, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 108 days.

(21) Appl. No.: 11/630,569

(22) PCT Filed: Jun. 18, 2005

(86) PCT No.: PCT/EP2005/006598

§ 371 (c)(1),
(2), (4) Date: Dec. 22, 2006

(87) PCT Pub. No.: WO2006/000358

PCT Pub. Date: Jan. 5, 2006

(65) Prior Publication Data

US 2007/0259919 A1 Nov. 8, 2007

(30) Foreign Application Priority Data

Jun. 25, 2004 (DE) .................. 10 2004 030 927

(51) Int. Cl.
C07D 401/04 (2006.01)
C07D 213/61 (2006.01)
C07D 417/04 (2006.01)
C07D 213/70 (2006.01)
C07D 213/86 (2006.01)
C07D 213/78 (2006.01)
A01N 43/40 (2006.01)

(52) U.S. Cl. .................. 424/405; 514/334; 514/341; 514/342; 544/333; 546/257; 546/270.4; 546/275.4

(58) Field of Classification Search .............. 424/405; 514/334, 341, 342; 544/333; 546/257, 270.4, 546/275.4

See application file for complete search history.

(56) References Cited

U.S. PATENT DOCUMENTS

| 4,469,696 | A | * | 9/1984 | Rosentreter et al. ..... 514/253.01 |
|---|---|---|---|---|
| 5,250,530 | A | | 10/1993 | Giencke et al. |
| 5,346,899 | A | | 9/1994 | Mueller et al. |
| 2004/0116429 | A1 | | 6/2004 | Grote et al. |
| 2006/0148764 | A1 | | 7/2006 | Gypser |

FOREIGN PATENT DOCUMENTS

| EP | 0 407 899 A2 | 1/1991 |
|---|---|---|
| EP | 0 588-146 A2 | 3/1994 |
| WO | WO-99/41255 A1 | 8/1999 |
| WO | WO-02/074753 A | 9/2002 |
| WO | WO-03/043993 A | 5/2003 |

OTHER PUBLICATIONS

Allen, Charles F. H. "Some reactions of delta ketonic nitriles" J. Am. Chem. Soc. 1925, 1733-1741.*

(Continued)

*Primary Examiner*—David J Blanchard
*Assistant Examiner*—Kortney L Klinkel
(74) *Attorney, Agent, or Firm*—Birch, Stewart, Kolasch & Birch, LLP

(57) ABSTRACT

The invention relates to 2-substituted pyridines of the formula I

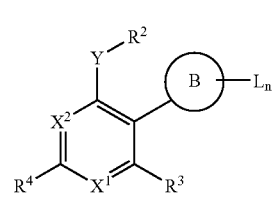

in which the index n and the substituents $R^1$ to $R^4$ and L are as defined in the description and
in each case one of the two ring members $X^1$, $X^2$ is N, the other is C—H or C-halogen;
Y is a group —CH—$R^1$—, —N—$R^1$—, —O— or —S— and

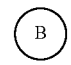

is five- or six-membered hetaryl comprising 1 to 3 heteroatoms selected from the group consisting of O, N and S or is phenyl,
and to processes for their preparation, intermediates for their preparation, pesticidal compositions and methods for controlling harmful fungi and animal pests using the compounds according to the invention.

11 Claims, No Drawings

OTHER PUBLICATIONS

Casson et. al., J. Chem. Soc. Perkin Trans. vol. pp. 1187-1191 (1994).
Sato et. al., J. Chem. Soc. Perkin Trans. vol. 1, pp. 2345-2349 (1996).
Evans et. al., Aust. J. Chem. vol. 43, pp. 733-740 (1990).
King et. al., J. Org. Chem. vol. 43, No. 2, pp. 358-360 (1978).
Miyaura et. al., J.C.S. Chem. Comm., vol. 866-867 (1979).
Miyachi et. al. Tetrahedron Letters, vol. 34, No. 51, pp. 8267-8270 (1993).
Booth et. al., Tetrahedron Letters, vol. 33, No. 3, pp. 413-416 (1992).

* cited by examiner

2-SUBSTITUTED PYRIDINES, PROCESSES FOR THEIR PREPARATION AND THEIR USE FOR CONTROLLING HARMFUL FUNGI

The present invention relates to 2-substituted pyridines of the formula I

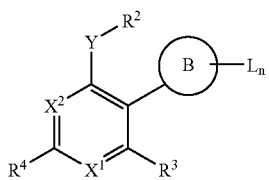

in which the indices and the substituents are as defined below:

$X^1$, $X^2$ in each case, one of the two ring members is N, the other is C—H or C-halogen;

Y is a group —CH—$R^1$—, —N—$R^1$—, —O— or —S—;

$R^1$, $R^2$ independently of one another are $C_1$-$C_8$-alkyl, $C_2$-$C_8$-alkenyl, $C_2$-$C_8$-alkynyl, $C_3$-$C_6$-cycloalkyl, $C_3$-$C_6$-halocycloalkyl, $R^1$ and $R^2$ for their part may be partially or fully halogenated or may carry one to four groups $R^v$:

$R^v$ is cyano, $C_1$-$C_6$-alkyl, $C_3$-$C_6$-cycloalkyl, $C_4$-$C_6$-cycloalkenyl, hydroxyl, $C_1$-$C_6$-alkoxy, $C_2$-$C_8$-alkenyloxy, $C_2$-$C_8$-alkynyloxy, $C_3$-$C_6$-cycloalkyloxy, $C_4$-$C_6$-cycloalkenyloxy, $C_1$-$C_6$-alkylthio, —C(=O)-A, —C(=O)—O-A, —C(=O)—N(A')A, C(A')(=N—OA), N(A')A, N(A')-C(=O)-A, N(A")-C(=O)—N(A')A, S(=O)$_m$-A, S(=O)$_m$—O-A or S(=O)$_m$—N(A')A or phenyl, where the phenyl moiety may carry one to three radicals selected from the group consisting of: halogen, $C_1$-$C_6$-alkyl, $C_2$-$C_6$-alkenyl; $C_2$-$C_6$-alkynyl, $C_3$-$C_6$-cycloalkyl, $C_1$-$C_6$-haloalkyl, $C_1$-$C_6$-alkoxy, cyano, nitro, —C(=O)-A, —C(=O)—O-A, —C(=O)—N(A')A, C(A')(=N—OA), N(A')A;

$R^1$ may additionally be hydrogen;

$R^1$ and $R^2$ may also, together with the nitrogen or carbon atom to which they are attached, form a saturated or unsaturated five- or six-membered ring which may be interrupted by an ether (—O—), carbonyl (C=O—), thio (—S—), sulfoxyl (—S[=O]—) or sulfenyl (—SO$_2$—) group or by a further amino —(—N($R^a$)— group, where $R^a$ is hydrogen or $C_1$-$C_6$-alkyl, and/or may comprise one or more substituents from the group consisting of halogen, $C_1$-$C_6$-alkyl, $C_1$-$C_6$-haloalkyl and oxy-$C_1$-$C_3$-alkyleneoxy; where $R^1$, $R^2$ are preferably as defined below:

$R^1$, $R^2$ independently of one another are $C_1$-$C_6$-alkyl, $C_2$-$C_6$-alkenyl, $C_2$-$C_6$-alkynyl, $C_3$-$C_6$-cycloalkyl, $C_3$-$C_6$-halocycloalkyl, where the aliphatic groups of the radical definitions of $R^1$ and $R^2$ for their part may be partially or fully halogenated or may carry one to four groups $R^v$:

$R^v$ is cyano, $C_3$-$C_6$-cycloalkyl, $C_4$-$C_6$-cycloalkenyl, hydroxyl, $C_1$-$C_6$-alkoxy, $C_2$-$C_8$-alkenyloxy, $C_2$-$C_8$-alkynyloxy, $C_3$-$C_6$-cycloalkyloxy, $C_4$-$C_6$-cycloalkenyloxy, $C_1$-$C_6$-alkylthio, —C(=O)-A, —C(=O)—O-A, —C(=O)—N(A')A, C(A')(=N—OA), N(A')A, N(A')-C(=O)-A, N(A")-C(=O)—N(A')A, S(=O)$_m$-A, S(=O)$_m$—O-A or S(=O)$_m$—N(A')A or phenyl, where the phenyl moiety may carry one to three radicals selected from the group consisting of: halogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_1$-$C_6$-alkoxy, cyano, nitro, —C(=O)-A, —C(=O)—O-A, —C(=O)—N(A')A, C(A')(=N—OA), N(A')A;

$R^1$ may additionally be hydrogen;

$R^1$ and $R^2$ may also, together with the nitrogen or carbon atom to which they are attached, form a saturated or unsaturated five- or six-membered ring which may be interrupted by an ether (—O—), carbonyl (C[=O]—), thio (—S—), sulfoxyl (—S[=O]—) or sulfenyl (—SO$_2$—) group or by a further amino —(—N($R^a$)— group, where $R^a$ is hydrogen or $C_1$-$C_6$-alkyl, and/or may comprise one or more substituents from the group consisting of halogen, $C_1$-$C_6$-alkyl, $C_1$-$C_6$-haloalkyl and oxy-$C_1$-$C_3$-alkyleneoxy;

$R^3$ is halogen, cyano, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy, $C_3$-$C_4$-alkenyloxy, $C_3$-$C_4$-alkynyloxy, $C_1$-$C_6$-alkylthio, di-($C_1$-$C_6$-alkyl) amino or $C_1$-$C_6$-alkylamino, where the alkyl, alkenyl and alkynyl radicals of $R^3$ may be substituted by halogen, cyano, nitro, $C_1$-$C_2$-alkoxy or $C_1$-$C_4$-alkoxycarbonyl;

$R^4$ is a five- or six-membered saturated, partially unsaturated or aromatic mono- or bicyclic heterocycle which comprises one to four heteroatoms from the group consisting of O, N and S which for its part may be partially or fully halogenated or may carry one to four groups $R^u$:

$R^u$ is cyano, $C_1$-$C_8$-alkyl, $C_2$-$C_8$-alkenyl, $C_2$-$C_8$-alkynyl, $C_1$-$C_6$-alkoxy, $C_3$-$C_6$-cycloalkyl, $C_2$-$C_8$-alkenyloxy, $C_2$-$C_8$-alkynyloxy, $C_4$-$C_6$-cycloalkenyl, $C_3$-$C_6$-cycloalkyloxy, $C_4$-$C_6$-cycloalkenyloxy, —C(=O)-A, —C(=O)—O-A, —C(=O)—N(A')A, C(A')(=N—OA), N(A')A, N(A')-C(=O)-A, N(A")-C(=O)—N(A') A, S(=O)$_m$-A, S(=O)$_m$—O-A or S(=O)$_m$, —N(A')A, where m, A, A', A" are as defined above;

$R^4$ may furthermore be:
cyano, C(=Z)O$R^a$, C(=Z)N$R^z R^b$, C(=Z)N$R^a$—N$R^z R^b$, C(=Z)$R^a$, C$R^a R^b$—O$R^z$,
C$R^a R^b$—N$R^z R^c$,
ON(=C$R^a R^b$), O—C(=Z)$R^a$,
N$R^a R^{b'}$, N$R^a$(C(=Z)$R^b$), N$R^a$(C(=Z)O$R^b$), N$R^a$(C(=Z)-N$R^z R^b$), N$R^a$(N=C$R^z R^b$),
N$R^a$—N$R^z R^b$, N$R^z$—O$R^a$, where
Z O, S, N$R^a$, NO$R^a$ or N—N$R^z R^c$;
$R^a$, $R^b$, $R^c$ independently of one another are hydrogen, $C_1$-$C_6$-alkyl, $C_2$-$C_6$-alkenyl, $C_2$-$C_6$-alkynyl, $C_3$-$C_6$-cycloalkyl or $C_4$-$C_6$-cycloalkenyl;
$R^{b'}$ has the same meanings as $R^b$, except for hydrogen;
$R^z$ has the same meanings as $R^a$ and may additionally be —CO—$R^a$;
where the aliphatic or alicyclic groups of the radical definitions of $R^a$, $R^b$, $R^c$ or $R^z$ for their part may be partially or fully halogenated or may carry one to four groups $R^w$:
$R^w$ is halogen, cyano, $C_1$-$C_8$-alkyl, $C_2$-$C_{10}$-alkenyl, $C_2$-$C_{10}$-alkynyl, $C_1$-$C_6$-alkoxy, $C_2$-$C_{10}$-alkenyloxy, $C_2$-$C_{10}$-alkynyloxy, $C_3$-$C_6$-cycloalkyl, $C_3$-$C_6$-cycloalkenyl, $C_3$-$C_6$-cycloalkoxy, $C_3$-$C_6$-cycloalkenyloxy, and where two of the radicals $R^a$, $R^b$, $R^c$ or $R^z$ together with the atoms, to which they are attached, may form a five- or six-membered saturated, partially unsaturated or aromatic heterocycle which comprises one to four heteroatoms from the group consisting of O, N and S;

is a five- or six-membered hetaryl which contains 1 to 3 heteroatoms selected from the group consisting of O, N and S or is phenyl;

n is an integer from 1 to 5;

L is halogen, cyano, cyanato (OCN), $C_1$-$C_8$-alkyl, $C_2$-$C_8$-alkenyl, $C_2$-$C_8$-alkynyl, $C_1$-$C_6$-alkoxy, $C_2$-$C_8$-alkenyloxy, $C_2$-$C_8$-alkynyloxy, $C_3$-$C_6$-cycloalkyl, $C_4$-$C_6$-cycloalkenyl, $C_3$-$C_6$-cycloalkyloxy, $C_4$-$C_6$-cycloalkenyloxy, nitro, —C(=O)-A, —C(=O)—O-A, —C(=O)—N(A')A, —C(=S)—N(A')A, C(A')(=N—OA), N(A')A, N(A')-C(=O)-A, N(A")-C(=O)—N(A')A, S(=O)$_m$-A, S(=O)$_m$—O-A or S(=O)$_m$—N(A')A, m is 0, 1 or 2;

We have found that this object is achieved by the 2-substituted pyridines I defined at the outset. Moreover, we have found processes for their preparation and compositions comprising them for controlling harmful fungi and their use for this purpose.

The compounds of the formula I can be obtained by different routes.

The compounds described can be prepared, for example, from appropriately substituted phenylacetonitriles II. These are known or obtainable analogously to the known substances.

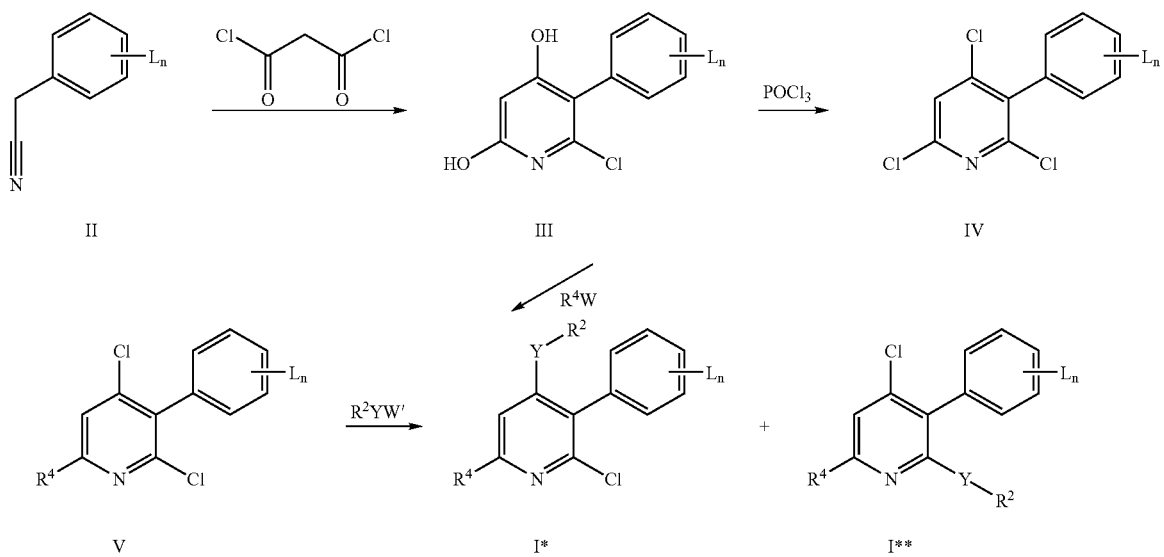

Scheme 1:

A, A', A" independently of one another are hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, phenyl, where the organic radicals may be partially or fully halogenated or may be substituted by nitro, cyanato, cyano or $C_1$-$C_4$-alkoxy; or A and A' together with the atoms to which they are attached are a five- or six-membered saturated, partially unsaturated or aromatic heterocycle which comprises one to four heteroatoms from the group consisting of O, N and S;

where the aliphatic groups of the radical definitions of L for their part may be partially or fully halogenated or may carry one to four groups $R^L$:

$R^L$ is cyano, $C_1$-$C_6$-alkoxy, $C_3$-$C_6$-cycloalkyl, $C_2$-$C_8$-alkenyloxy, $C_2$-$C_8$-alkynyloxy, $C_4$-$C_6$-cycloalkenyl, $C_3$-$C_6$-cycloalkyloxy, $C_4$-$C_6$-cycloalkenyloxy, —C(=O)-A, —C(=O)—O-A, —C(=O)—N(A')A, C(A')(=N—OA), N(A')A, N(A')-C(=O)-A, N(A")-C(=O)—N(A')A, S(=O)$_m$-A, S(=O)$_m$—O-A or S(=O)$_m$—N(A')A.

2-Substituted pyrimidines having fungicidal action are already known from the literature (EP-A 407899, WO-A 02/074753 and WO-A 03/043993).

However, the activity of the abovementioned pyrimidines (pyridines) is in many cases unsatisfactory. Accordingly, it was an object of the present invention to provide further compounds having fungicidal action.

Using malonyl chloride, the phenylacetonitriles II can be converted into the dihydroxypyridine derivatives III (see Scheme 1). This reaction can be carried out in the absence of a solvent, but it is also possible to employ a solvent which is inert under the reaction conditions and in which the reactants are sufficiently soluble. The reaction temperature can be between −20° C. and 150° C. and is preferably between 0° C. and 100° C.

The dihydroxypyridines III obtainable in this manner can then be chlorinated using customary methods to give the trichloropyridines IV. The use of phosphorus oxychloride, if appropriate with addition of an amine such as diethylaniline, an amine hydrochloride or dimethylformamide, has been found to be particularly suitable. Usually, it is advantageous to carry out the reaction at elevated temperature to increase the conversion rate.

The trichloropyridines IV can then be substituted further by different routes. It has been found that frequently, the regioselectivity depends to an unexpected degree on the chosen co-reactants and reaction conditions. In the route shown in Scheme 1, the substituent ($R^4$) is initially introduced into the 6-position and the amine is then attached nucleophilically in the 2- or 4-position. However, if required by the relative reactivities of the reaction centers, the order of these reactions may also be changed.

For introducing a heterocyclic radical $R^4$ in the 6-position it is possible to use the heterocycle (such as, for example, pyrazole or triazole) directly, depending on its nucleophilicity. In these cases, an auxiliary base is usually employed; here, W is hydrogen. It is also possible to introduce heterocyclic substituents via palladium- or nickel-catalyzed reactions. In these cases, the heterocycle carries a suitable organometallic leaving group. Here, W is an organometallic boron, tin (as in Synthesis Examples A to C), zinc, magnesium or iron radical.

Other important intermediates of the formula V can be prepared as in Scheme 2. Via nucleophilic substitution, it is possible to introduce, in the 6-position, a thiolate group ($C_1$-$C_6$-alkylthio) which can be oxidized to $C_1$-$C_6$-alkylsulfenyl ($C_1$-$C_6$-alkylS[=O]$_2$—) and thus be converted into a leaving group for further exchange reactions. Hydrogen peroxide or peracids of organic carboxylic acids have been found to be particularly suitable oxidizing agents. However, the oxidation also be carried out using, for example, selenium dioxide. In this manner it is possible to introduce, for example, cyanides (nitriles) into the 6-position which can then be reacted further by known methods to give, for example, amides, amidoximes or amidines. Amidoximes, for example, can be prepared from the nitriles and hydroxylamine or O-alkylated hydroxylamines.

5-bromo-substituted pyridine derivatives can be prepared as shown in Scheme 2, for example by metallation and halogenation from the trichloropyridine IV and analogous substances. Via the alkyl thiolate Va and oxidation to Vb, IV' can then be converted into the nitrile Vc. This can then be used as an intermediate, for example for the synthesis of amides, esters and amidoximes (such as Vc). To this end, the customary methods for converting these functional groups are employed. To obtain O-alkylated amidoximes, it is possible either to alkylate Vd (for example with methyl iodide and a base such as sodium hydride or potassium tert-butoxide in dimethyl sulfoxide) or to react a nitrile such as Vc directly with an O-alkylated hydroxylamine.

Scheme 2

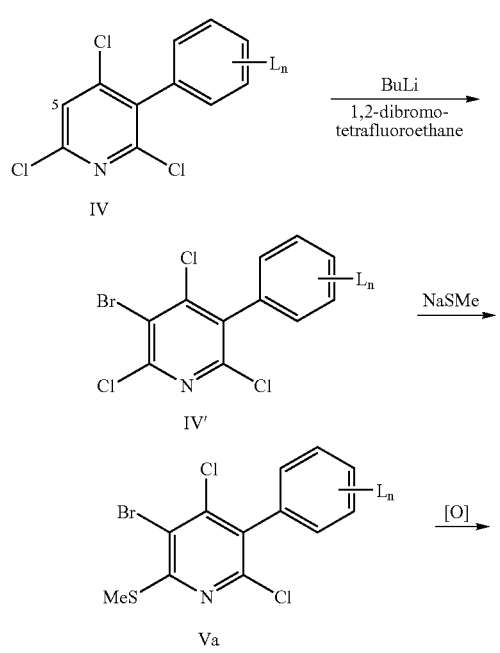

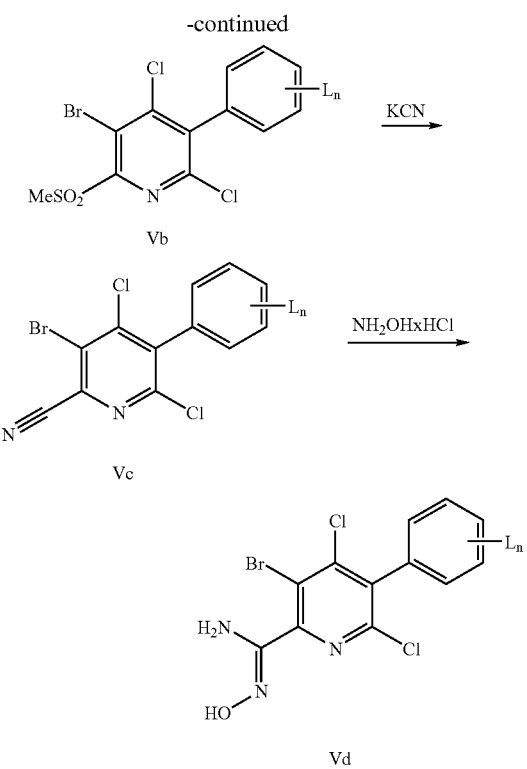

Using appropriate nucleophiles (amines; alcohols, mercaptans), Vc and Vd and the intermediates derived therefrom (V in general) can then be converted as described above into the active compounds I where Y is —N—R$^1$—, —O— or —S— (see Scheme 3). The reaction temperature can be from 0° C. to 200° C. In most cases, the reaction will proceed faster at slightly elevated temperature. If required, the reaction is carried out at elevated pressure to achieve this temperature.

If Y is a radical —CH—R$^1$ or R$^3$ is a radical attached via carbon, these radicals are introduced using organometallic compounds and transition metal catalysis, such as Ni- or Pd-catalysis. In some cases it may be advisable to reverse the order and to introduce the substituent R$^3$ first.

Scheme 3:

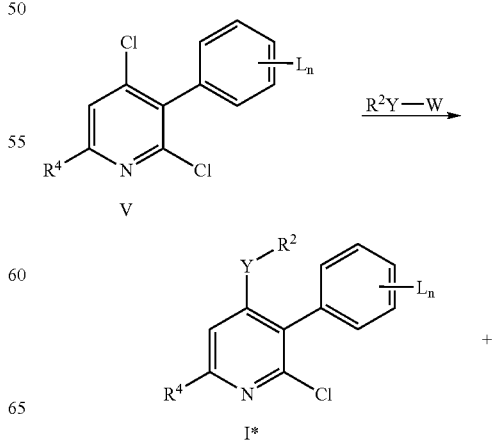

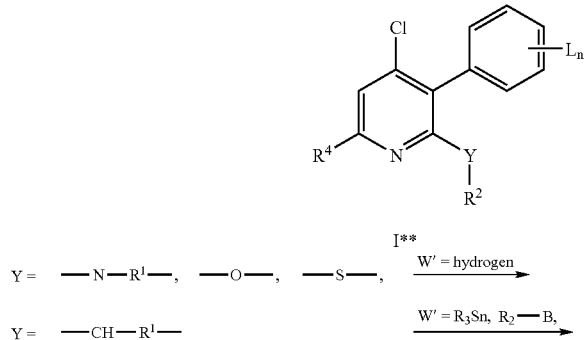

In this case, the formula $R^2Y$—W' represents, for example, a compound of the formula: $W'=(R^2CH(R^1))_n\text{-}M^n$. M is a metal ion of valency n, such as, for example, B, Zn, Mg or Sn. This reaction can be carried out, for example, analogously to the following methods: J. Chem. Soc. Perkin Trans. 1, (1994) 1187, ibid. 1, (1996) 2345; WO-A 99/41255; Aust. J. Chem., 43 (1990), 733; J. Org. Chem. 43 (1978), 358; J. Chem. Soc. Chem. Commun. 866 (1979); Tetrahedron Lett., 34 (1993), 8267; ibid. 33 (1992), 413.

What was said above also applies to the preparation of compounds in which $R^3$ is an alkyl group. As illustrated in more detail above, such an alkyl group ($R^3$) can be prepared using organometallic compounds of the formula $(R^3)_n\text{-}M^n$ where M is as defined above. If $R^3$ is a cyano group or an alkoxy substituent, the radical $R^3$ can be introduced by reaction with alkali metal cyanides and alkali metal alkoxides, respectively.

In the definitions of the symbols given in the formulae above, collective terms were used which are generally representative for the following substituents:

halogen: fluorine, chlorine, bromine and iodine;

alkyl and the alkyl moieties of, for example, alkoxy, alkylamino, alkoxycarbonyl: saturated straight-chain or branched hydrocarbon radicals having 1 to 4, 6 or 8 carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 4, 6 or 8 carbon atoms (as mentioned above), where in these groups some or all of the hydrogen atoms may be replaced by halogen atoms as mentioned above, for example $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl;

alkenyl: unsaturated straight-chain or branched hydrocarbon radicals having 2 to 4, 6 or 8 carbon atoms and a double bond in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkadienyl: unsaturated straight-chain or branched hydrocarbon radicals having 4 to 8 carbon atoms and two double bonds in any position;

haloalkenyl: unsaturated straight-chain or branched hydrocarbon radicals having 2 to 8 carbon atoms and a double bond in any position (as mentioned above), where in these groups some or all of the hydrogen atoms may be replaced by halogen atoms as mentioned above, in particular by fluorine, chlorine and bromine;

alkynyl: straight-chain or branched hydrocarbon groups having 2 to 8 carbon atoms and a triple bond in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl: mono- or bicyclic saturated hydrocarbon groups having 3 to 6 carbon ring members, for example $C_3$-$C_6$-cycloalkyl such as cyclopropyl, cyclobutyl, cyclopentyl, cyclohexyl;

five- or six-membered saturated, partially unsaturated or aromatic heterocycle which comprises one to four heteroatoms from the group consisting of O, N and S: for example 2-tetrahydrofuryl, 3-tetrahydrofuryl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

ring system which is optionally formed by $R^1$ and $R^2$ or by A and A' together with the nitrogen to which they are attached: for example pyrrolidine, morpholine, piperidine or tetrahydropyrazole.

The scope of the present invention includes the (R) and (S) isomers and the racemates of compounds of the formula I having chiral centers.

Hereinbelow, the embodiments of the invention are described in more detail.

With a view to the intended use of the pyridines of the formula I, particular preference is given to the following meanings of the substituents, in each case on their own or in combination:

Preference is given to compounds I in which $R^1$ is $C_1$-$C_6$-alkyl, $C_1$-$C_6$-haloalkyl, $C_2$-$C_6$-alkenyl, $C_2$-$C_6$-alkynyl or $C_3$-$C_6$-cycloalkyl and $R^2$ is hydrogen.

Especially preferred are compounds I in which $R^1$ is $C_1$-$C_6$-haloalkyl, $C_2$-$C_6$-alkenyl or $C_1$-$C_6$-alkyl branched in the α-position. Particular preference is given to the compounds I in which $R^1$ is as defined above and $R^2$ is hydrogen.

In addition, preference is given to compounds I in which $R^1$ is $C_1$-$C_4$-haloalkyl and $R^2$ is hydrogen.

Moreover, preference is given to compounds I in which $R^1$ and $R^2$ together with the nitrogen to which they are attached form a five- or six-membered ring which may be interrupted by an oxygen atom and may carry one or two $C_1$-$C_6$-alkyl substituents.

Especially preferred are groups $NR^1R^2$ (corresponds to —NCH($R^1$)—$R^2$) such as pyrrolidines or piperidines which are methylated—in particular in the α-position. Preference is furthermore given to 4-methylpiperidine.

Preference is furthermore given to pyridines in which the substituent $R^2$—Y— has the following meanings:

Y is a group —CH—$R^1$ or —N—$R^1$ where $R^1$ is hydrogen and $R^2$ is $C_3$-$C_8$-alkenyl, $C_3$-$C_8$-alkynyl, $C_3$-$C_6$-haloalkyl or $C_3$-$C_8$-alkyl branched in the α-position.

Particularly preferred are also compounds I in which $R^3$ is $C_1$-$C_4$-alkyl which may be substituted by halogen.

Moreover, particular preference is given to compounds I in which $R^3$ is halogen, cyano, $C_1$-$C_4$-alkyl or $C_1$-$C_4$-alkoxy.

Especially preferred are compounds I in which $R^3$ is methyl, cyano, methoxy or, in particular, chlorine.

Preference is furthermore given to compounds I in which $R^4$ is pyrrole, pyrazole, imidazole, 1,2,3-triazole, 1,2,4-triazole, tetrazole, oxazole, isoxazole, 1,3,4-oxadiazole, furan, thiophene, thiazole, isothiazole, pyridine, pyrimidine, pyrazine, pyridazine, 1,2,3-triazine, 1,2,4-triazine, 1-pyridin(1,2,-dihydro)-2-one or 1-pyrrolidone, where the heterocycle may be attached to the pyridine ring via C or N and may carry up to three substituents $R^u$. This preference applies both in combination with the broad definition of $R^u$ given in claim 1 and with the narrower definition of $R^u$ below: halogen, cyano, $C_1$-$C_8$-alkyl, $C_1$-$C_8$-haloalkyl, $C_1$-$C_6$-alkoxy, —C(=O)-A, —C(=O)—O-A, —C(=O)—N(A')A, C(A')(=N—OA), N(A')A, N(A')-C(=O)-A.

Particularly preferred are compounds I in which $R^4$ is 1-pyrazolyl, 1-[1,2,4]triazolyl, 2-thiazolyl, 2-pyridinyl, 2-pyrimidinyl, 3-pyridazinyl, 1-pyridin(1,2-dihydro)-2-onyl or 1-pyrrolidonyl. This preference applies both in combination with the broad definition of $R^u$ given in claim 1 and with the narrower definition of $R^u$ below: halogen, cyano, $C_1$-$C_8$-alkyl, $C_1$-$C_8$-haloalkyl, $C_1$-$C_6$-alkoxy, —C(=O)-A, —C(=O)—O-A, —C(=O)—N(A')A, C(A')(=N—OA), N(A')A, N(A')-C(=O)-A.

Preference is furthermore given to compounds I in which $R^4$ is pyrazolyl or [1,2,4]triazolyl.

Especially preferred are compounds I in which $R^4$ is 2-pyrimidinyl. This preference applies both in combination with the broad definition of $R^u$ given in claim 1 and with the narrower definition of $R^u$ below: halogen, cyano, $C_1$-$C_8$-alkyl, $C_1$-$C_8$-haloalkyl, $C_1$-$C_6$-alkoxy, —C(=O)-A, —C(=O)—O-A, —C(=O)—N(A')A, C(A')(=N—OA), N(A')A, N(A')-C(=O)-A.

Preference is also given to compounds I in which $R^4$ is cyano, C(=O)$NR^zR^b$, C(=$NOR^a$)$NR^zR^b$, C(=$NOR^b$)$R^a$, C(=N—$NR^zR^b$)$R^a$ or $CR^aR^b$—$NR^zR^c$, ON(=$CR^aR^b$), $NR^a$(C(=O)$R^b$), $NR^a$(C(=O)$OR^b$), $NR^a$(N=$CR^cR^b$) or $NR^z$—$OR^a$.

Moreover, preference is given to compounds I in which $R^4$ is C(=Z)$OR^a$, C(=Z)$NR^zR^b$ or C(=Z)$R^a$ and Z is O, $NR^a$ or $NOR^a$.

Especially preferred are compounds I in which $R^4$ is C(=O)$NR^zR^b$ or C(=N—$OCH_3$)$NR^zR^b$ and preferably C(=O)$NH_2$ or C(=N—$OCH_3$)$NH_2$.

Preference is furthermore given to compounds I in which $R^4$ is C(=NH)$NR^zR^b$ and $R^z$ is an acyl substituent: —CO—$R^a$.

(B)

is particularly preferably five-membered hetaryl which comprises 1 to 3 heteroatoms selected from the group consisting of O, N or S or is pyridyl or particularly preferably phenyl.

Especially preferred are pyridines I where the substituents

L ($L^1$ to $L^5$) are as defined below:

L is halogen, cyano, methyl, methoxy, —C(=O)—O-A, —C(=O)—N(A')A, —C(=S)—N(A')A, C(A')(=N—OA), N(A')A, N(A')-C(=O)-A, A, A' independently of one another are hydrogen, $C_1$-$C_6$-alkyl, $C_2$-$C_6$-alkenyl, $C_2$-$C_6$-alkynyl, phenyl, where the organic radicals may be partially or fully halogenated or may be substituted by $C_1$-$C_4$-alkoxy; or A and A' together with the atoms to which they are attached are a five- or six-membered saturated heterocycle which comprises one or two heteroatoms from the group consisting of O, N and S.

Moreover, preference is given to pyridines I in which the group substituted by $L_n$ is B

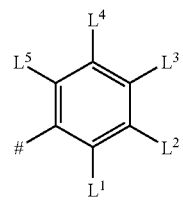

B in which # is the point of attachment to the pyridine skeleton and $L^1$ is fluorine, chlorine, $CH_3$ or $CF_3$;

$L^2$, $L^4$ independently of one another are hydrogen, $CH_3$ or fluorine;

$L^3$ is hydrogen, fluorine, chlorine, bromine, cyano, $CH_3$, $SCH_3$, $OCH_3$, $SO_2CH_3$, CO—$NH_2$, CO—$NHCH_3$, CO—$NHC_2H_5$, CO—$N(CH_3)_2$, CS—$NH_2$, CS—$NHCH_3$, CS—$N(CH_3)_2$, NH—C(=O)$CH_3$, N($CH_3$)—C(=O)$CH_3$ or COO$CH_3$ and $L^5$ is hydrogen, fluorine, chlorine or $CH_3$.

Preference is furthermore given to 2-substituted pyridines of the formula I'

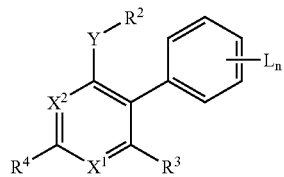

I' where

Y is a group —CH—$R^1$—, —N—$R^1$— or —O—;

$R^1$, $R^2$ independently of one another are $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl or $C_2$-$C_6$-haloalkynyl;

$R^1$ may additionally be hydrogen;

$R^1$ and $R^2$ may also, together with the nitrogen atom to which they are attached, form a saturated or unsaturated five- or six-membered ring which may be interrupted by an ether (—O—) or by a further amino —(—N($R^a$))— group, where $R^a$ is hydrogen or $C_1$-$C_6$-alkyl, and/or may comprise one or more substituents from the group consisting of halogen, $C_1$-$C_6$-alkyl, $C_1$-$C_6$-haloalkyl and oxy-$C_1$-$C_3$-alkyleneoxy;

$R^3$ is halogen, cyano, $C_1$-$C_4$-alkyl, $C_1$-$C_4$-alkoxy or $C_1$-$C_4$-haloalkyl;

$R^4$ is pyrrole, pyrazole, imidazole, 1,2,3-triazole, 1,2,4-triazole, tetrazole, oxazole, isoxazole, 1,3,4-oxadiazole, furan, thiophene, thiazole, isothiazole, pyridine, pyrimidine, pyrazine, pyridazine, 1,2,3-triazine, 1,2,4-triazine, 1-pyridin(1,2-dihydro)-2-one or 1-pyrrolidone, where the heterocycle may be attached via C or N to the pyridine ring and may carry up to three substituents $R^u$.

$R^u$ is halogen, cyano, $C_1$-$C_8$-alkyl, $C_1$-$C_6$-alkoxy, —C(=O)-A, —C(=O)—O-A, —C(=O)—N(A')A, C(A')(=N—OA), N(A')A, N(A')-C(=O)-A, or cyano, C(=O)$NR^zR^b$, C(=$NOR^a$)$NR^zR^b$, C(=$NOR^b$)$R^a$, C(=N—$NR^zR^b$)$R^a$ or $CR^aR^b$—$NR^zR^c$, ON(=$CR^aR^b$), $NR^a$(C(=O)$R^b$), $NR^a$(C(=O)$OR^b$), $NR^a$(N=$CR^cR^b$) or $NR^z$—$OR^a$;

n is an integer from 1 to 3 where at least one substituent L is located in the ortho-position on the phenyl ring;

L is halogen, cyano, methyl, methoxy, —C(=O)—O-A, —C(=O)—N(A')A, —C(=S)—N(A')A, C(A')(=N—OA), N(A')A, N(A')-C(=O)-A, A, A' independently of one another are hydrogen, $C_1$-$C_6$-alkyl, $C_2$-$C_6$-alkenyl, $C_2$-$C_6$-alkynyl, phenyl, where the organic radicals may be partially or fully halogenated or may be substituted by $C_1$-$C_4$-alkoxy; or A and A' together with the atoms to which they are attached are a five- or six-membered saturated heterocycle which comprises one or two heteroatoms from the group consisting of O, N and S;

where the aliphatic groups of the radical definitions of L for their part may be partially or fully halogenated.

In particular with a view to their use, preference is given to compounds I compiled in the tables below. Moreover, the groups mentioned for a substituent in the tables are per se, independently of the combination in which they are mentioned, a particularly preferred embodiment of the substituent in question.

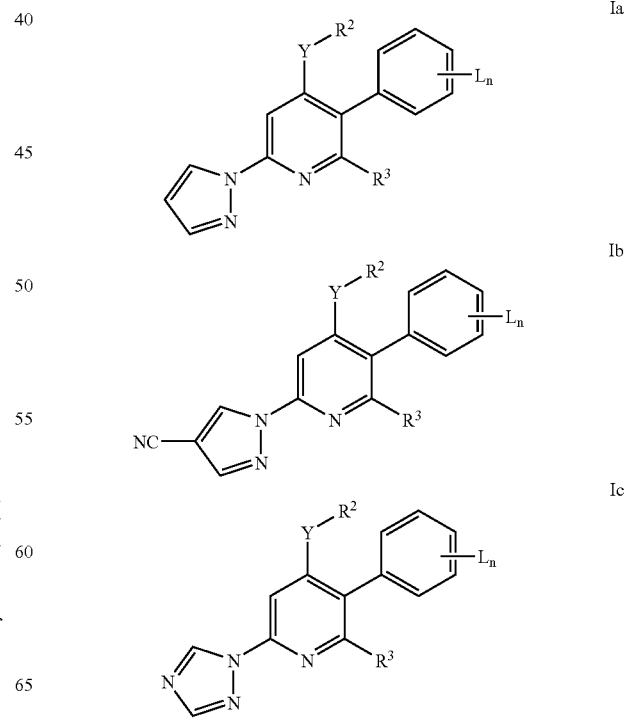

-continued

Id

Ie

If

Ig

Ih

Ii

-continued

Ij

Ik

IL

Im

In

Io

-continued

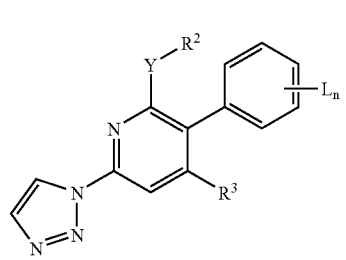
Ip

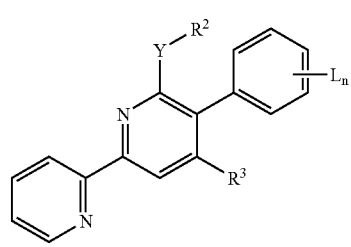
Iq

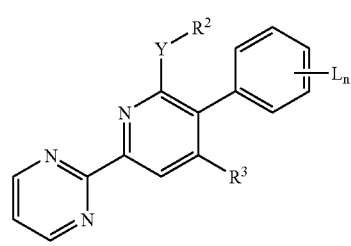
Ir

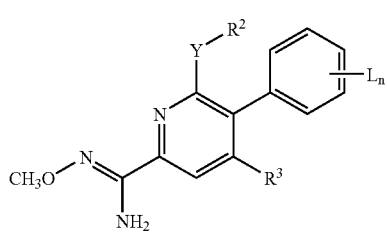
Is

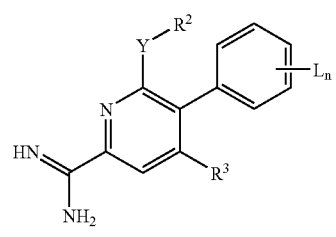
It

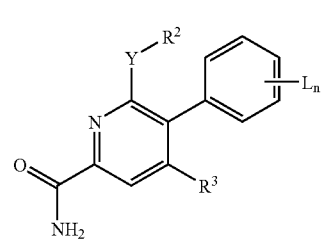
Iu

-continued

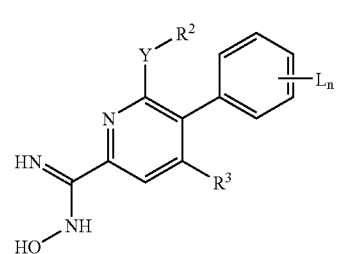
Iv

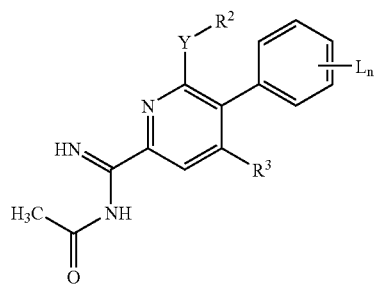
Iw

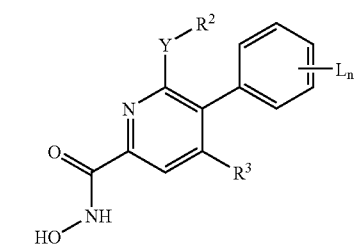
Ix

Table 1
  Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 6-chloro, $R^3$ is methyl and $YR^2$ for each compound corresponds to one row of Table A Table 2
  Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro, $R^3$ is methyl and $YR^2$ for each compound corresponds to one row of Table A Table 3
  Compounds of the formulae Ia, Ib, Ic, Id, Ie, If, Ig, Ih, Ii, Ij, Ik, IL, Im, In, Io, Ip, Iq, Ir, Is It, Iu, Iv, Iw and Ix in which $L_n$ is 2,6-dichloro, $R^3$ is methyl and $YR^2$ for each compound corresponds to one row of Table A Table 4
  Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 6-methyl, $R^3$ is methyl and $YR^2$ for each compound corresponds to one row of Table A Table 5
  Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4,6-trifluoro, $R^3$ is methyl and $YR^2$ for each compound corresponds to one row of Table A Table 6
  Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-fluoro, $R^3$ is methyl and $YR^2$ for each compound corresponds to one row of Table A Table 7
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 4-methoxycarbonyl, $R^3$ is methyl and $YR^2$ for each compound corresponds to one row of Table A Table 8
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 4-CN, $R^3$ is methyl and $YR^2$ for each compound corresponds to one row of Table A Table 9
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4,5-trifluoro, $R^3$ is methyl and $YR^2$ for each compound corresponds to one row of Table A Table 10
Compounds of the formulae Ia, Ib, Ic, Id, Ie, If, Ig, Ih, Ii, Ij, Ik, IL, Im, In, Io, Ip, Iq, Ir, Is It, Iu, Iv, Iw and Ix in which $L_n$ is 2,4-dichloro, $R^3$ is methyl and $YR^2$ for each compound corresponds to one row of Table A Table 11
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, $R^3$ is methyl and $YR^2$ for each compound corresponds to one row of Table A Table 12
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, $R^3$ is methyl and $YR^2$ for each compound corresponds to one row of Table A Table 13
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4-difluoro, $R^3$ is methyl and $YR^2$ for each compound corresponds to one row of Table A Table 14
Compounds of the formulae Ia, Ib, Ic, Id, Ie, If, Ig, Ih, Ii, Ij, Ik, IL, Im, In, Io, Ip, Iq, Ir, Is It, Iu, Iv, Iw and Ix in which $L_n$ is 2-fluoro-4-chloro, $R^3$ is methyl and $YR^2$ for each compound corresponds to one row of Table A Table 15
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro-4-fluoro, $R^3$ is methyl and $YR^2$ for each compound corresponds to one row of Table A Table 16
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,3-difluoro, $R^3$ is methyl and $YR^2$ for each compound corresponds to one row of Table A Table 17
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,5-difluoro, $R^3$ is methyl and $YR^2$ for each compound corresponds to one row of Table A Table 18
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,3,4-trifluoro, $R^3$ is methyl and $YR^2$ for each compound corresponds to one row of Table A Table 19
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, $R^3$ is methyl and $YR^2$ for each compound corresponds to one row of Table A Table 20
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4-dimethyl, $R^3$ is methyl and $YR^2$ for each compound corresponds to one row of Table A Table 21
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl-4-chloro, $R^3$ is methyl and $YR^2$ for each compound corresponds to one row of Table A Table 22
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro-4-methyl, $R^3$ is methyl and $YR^2$ for each compound corresponds to one row of Table A Table 23
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-dimethyl, $R^3$ is methyl and $YR^2$ for each compound corresponds to one row of Table A Table 24
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4,6-trimethyl, $R^3$ is methyl and $YR^2$ for each compound corresponds to one row of Table A Table 25
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro-4-cyano, $R^3$ is methyl and $YR^2$ for each compound corresponds to one row of Table A Table 26
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro-4-methyl, $R^3$ is methyl and $YR^2$ for each compound corresponds to one row of Table A Table 27
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro-4-methoxycarbonyl, $R^3$ is methyl and $YR^2$ for each compound corresponds to one row of Table A Table 28
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-methoxy, $R^3$ is methyl and $YR^2$ for each compound corresponds to one row of Table A Table 29
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-methyl, $R^3$ is methyl and $YR^2$ for each compound corresponds to one row of Table A Table 30
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-methoxycarbonyl, $R^3$ is methyl and $YR^2$ for each compound corresponds to one row of Table A Table 31
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-bromo, $R^3$ is methyl and $YR^2$ for each compound corresponds to one row of Table A Table 32
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-cyano, $R^3$ is methyl and $YR^2$ for each compound corresponds to one row of Table A Table 33
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro, 4-methoxy, $R^3$ is methyl and $YR^2$ for each compound corresponds to one row of Table A Table 34
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 3-methyl, $R^3$ is methyl and $YR^2$ for each compound corresponds to one row of Table A Table 35
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,5-dimethyl, $R^3$ is methyl and $YR^2$ for each compound corresponds to one row of Table A Table 36
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-cyano, $R^3$ is methyl and $YR^2$ for each compound corresponds to one row of Table A Table 37
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-bromo, $R^3$ is methyl and $YR^2$ for each compound corresponds to one row of Table A Table 38
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 5-fluoro, $R^3$ is methyl and $YR^2$ for each compound corresponds to one row of Table A Table 39
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-methoxy, $R^3$ is methyl and $YR^2$ for each compound corresponds to one row of Table A Table 40
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-methoxycarbonyl, $R^3$ is methyl and $YR^2$ for each compound corresponds to one row of Table A Table 41
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,5-dimethyl, 4-bromo, $R^3$ is methyl and $YR^2$ for each compound corresponds to one row of Table A Table 42
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 4-bromo, $R^3$ is methyl and $YR^2$ for each compound corresponds to one row of Table A Table 43
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 4-methoxy, $R^3$ is methyl and $YR^2$ for each compound corresponds to one row of Table A Table 44
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 5-methyl, $R^3$ is methyl and $YR^2$ for each compound corresponds to one row of Table A Table 45
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is pentafluoro, $R^3$ is methyl and $YR^2$ for each compound corresponds to one row of Table A Table 46
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 5-fluoro, 4-methoxy, $R^3$ is methyl and $YR^2$ for each compound corresponds to one row of Table A Table 47
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 5-fluoro, $R^3$ is methyl and $YR^2$ for each compound corresponds to one row of Table A Table 48
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 6-chloro, $R^3$ is chlorine and $YR^2$ for each compound corresponds to one row of Table A Table 49
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro, $R^3$ is chlorine and $YR^2$ for each compound corresponds to one row of Table A Table 50
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-dichloro, $R^3$ is chlorine and $YR^2$ for each compound corresponds to one row of Table A Table 51
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 6-methyl, $R^3$ is chlorine and $YR^2$ for each compound corresponds to one row of Table A Table 52
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4,6-trifluoro, $R^3$ is chlorine and $YR^2$ for each compound corresponds to one row of Table A Table 53
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-fluoro, $R^3$ is chlorine and $YR^2$ for each compound corresponds to one row of Table A Table 54
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 4-methoxycarbonyl, $R^3$ is chlorine and $YR^2$ for each compound corresponds to one row of Table A Table 55
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 4-CN, $R^3$ is chlorine and $YR^2$ for each compound corresponds to one row of Table A Table 56
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4,5-trifluoro, $R^3$ is chlorine and $YR^2$ for each compound corresponds to one row of Table A Table 57
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4-dichloro, $R^3$ is chlorine and $YR^2$ for each compound corresponds to one row of Table A Table 58
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, $R^3$ is chlorine and $YR^2$ for each compound corresponds to one row of Table A Table 59
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, $R^3$ is chlorine and $YR^2$ for each compound corresponds to one row of Table A Table 60
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4-difluoro, $R^3$ is chlorine and $YR^2$ for each compound corresponds to one row of Table A Table 61
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro-4-chloro, $R^3$ is chlorine and $YR^2$ for each compound corresponds to one row of Table A Table 62
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro-4-fluoro, $R^3$ is chlorine and $YR^2$ for each compound corresponds to one row of Table A Table 63
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,3-difluoro, $R^3$ is chlorine and $YR^2$ for each compound corresponds to one row of Table A Table 64
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,5-difluoro, $R^3$ is chlorine and $YR^2$ for each compound corresponds to one row of Table A Table 65
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,3,4-trifluoro, $R^3$ is chlorine and $YR^2$ for each compound corresponds to one row of Table A Table 66
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, $R^3$ is chlorine and $YR^2$ for each compound corresponds to one row of Table A Table 67
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4-dimethyl, $R^3$ is chlorine and $YR^2$ for each compound corresponds to one row of Table A Table 68
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl-4-chloro, $R^3$ is chlorine and $YR^2$ for each compound corresponds to one row of Table A Table 69
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro-4-methyl, $R^2$ is chlorine and $YR^2$ for each compound corresponds to one row of Table A Table 70
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-dimethyl, $R^3$ is chlorine and $YR^2$ for each compound corresponds to one row of Table A Table 71
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4,6-trimethyl, $R^3$ is chlorine and $YR^2$ for each compound corresponds to one row of Table A Table 72
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro-4-cyano, $R^3$ is chlorine and $YR^2$ for each compound corresponds to one row of Table A Table 73
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro-4-methyl, $R^3$ is chlorine and $YR^2$ for each compound corresponds to one row of Table A Table 74
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro-4-methoxycarbonyl, $R^3$ is chlorine and $YR^2$ for each compound corresponds to one row of Table A Table 75
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-methoxy, $R^3$ is chlorine and $YR^2$ for each compound corresponds to one row of Table A Table 76
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-methyl, $R^3$ is chlorine and $YR^2$ for each compound corresponds to one row of Table A Table 77
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-methoxycarbonyl, $R^3$ is chlorine and $YR^2$ for each compound corresponds to one row of Table A Table 78
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-bromo, $R^3$ is chlorine and $YR^2$ for each compound corresponds to one row of Table A Table 79
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-cyano, $R^3$ is chlorine and $YR^2$ for each compound corresponds to one row of Table A Table 80
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro, 4-methoxy, $R^3$ is chlorine and $YR^2$ for each compound corresponds to one row of Table A Table 81
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 3-methyl, $R^3$ is chlorine and $YR^2$ for each compound corresponds to one row of Table A Table 82
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,5-dimethyl, $R^3$ is chlorine and $YR^2$ for each compound corresponds to one row of Table A Table 83
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-cyano, $R^3$ is chlorine and $YR^2$ for each compound corresponds to one row of Table A Table 84
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-bromo, $R^3$ is chlorine and $YR^2$ for each compound corresponds to one row of Table A Table 85
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 5-fluoro, $R^3$ is chlorine and $YR^2$ for each compound corresponds to one row of Table A Table 86
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-methoxy, $R^3$ is chlorine and $YR^2$ for each compound corresponds to one row of Table A Table 87
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-methoxycarbonyl, $R^3$ is chlorine and $YR^2$ for each compound corresponds to one row of Table A Table 88
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,5-dimethyl, 4-bromo, $R^3$ is chlorine and $YR^2$ for each compound corresponds to one row of Table A Table 89
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 4-bromo, $R^3$ is chlorine and $YR^2$ for each compound corresponds to one row of Table A Table 90
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 4-methoxy, $R^3$ is chlorine and $YR^2$ for each compound corresponds to one row of Table A Table 91
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 5-methyl, $R^3$ is chlorine and $YR^2$ for each compound corresponds to one row of Table A Table 92
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is pentafluoro, $R^3$ is chlorine and $YR^2$ for each compound corresponds to one row of Table A Table 93
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 5-fluoro, 4-methoxy, $R^3$ is chlorine and $YR^2$ for each compound corresponds to one row of Table A Table 94
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 5-fluoro, $R^3$ is chlorine and $YR^2$ for each compound corresponds to one row of Table A Table 95
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 6-chloro, $R^3$ is methoxy and $YR^2$ for each compound corresponds to one row of Table A Table 96
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro, $R^3$ is methoxy and $YR^2$ for each compound corresponds to one row of Table A Table 97
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-dichloro, $R^3$ is methoxy and $YR^2$ for each compound corresponds to one row of Table A Table 98
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 6-methyl, $R^3$ is methoxy and $YR^2$ for each compound corresponds to one row of Table A Table 99
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4,6-trifluoro, $R^3$ is methoxy and $YR^2$ for each compound corresponds to one row of Table A Table 100
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-fluoro, $R^3$ is methoxy and $YR^2$ for each compound corresponds to one row of Table A Table 101
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 4-methoxycarbonyl, $R^3$ is methoxy and $YR^2$ for each compound corresponds to one row of Table A Table 102
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 4-CN, $R^3$ is methoxy and $YR^2$ for each compound corresponds to one row of Table A Table 103
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4,5-trifluoro, $R^3$ is methoxy and $YR^2$ for each compound corresponds to one row of Table A Table 104
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4-dichloro, $R^3$ is methoxy and $YR^2$ for each compound corresponds to one row of Table A Table 105
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, $R^3$ is methoxy and $YR^2$ for each compound corresponds to one row of Table A Table 106
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, $R^3$ is methoxy and $YR^2$ for each compound corresponds to one row of Table A Table 107
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4-difluoro, $R^3$ is methoxy and $YR^2$ for each compound corresponds to one row of Table A Table 108
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro-4-chloro, $R^3$ is methoxy and $YR^2$ for each compound corresponds to one row of Table A Table 109
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro-4-fluoro, $R^3$ is methoxy and $YR^2$ for each compound corresponds to one row of Table A Table 110
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,3-difluoro, $R^3$ is methoxy and $YR^2$ for each compound corresponds to one row of Table A Table 111
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,5-difluoro, $R^3$ is methoxy and $YR^2$ for each compound corresponds to one row of Table A Table 112
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,3,4-trifluoro, $R^3$ is methoxy and $YR^2$ for each compound corresponds to one row of Table A Table 113
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, $R^3$ is methoxy and $YR^2$ for each compound corresponds to one row of Table A Table 114
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4-dimethyl, $R^3$ is methoxy and $YR^2$ for each compound corresponds to one row of Table A Table 115
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl-4-chloro, $R^3$ is methoxy and $YR^2$ for each compound corresponds to one row of Table A Table 116
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro-4-methyl, $R^3$ is methoxy and $YR^2$ for each compound corresponds to one row of Table A Table 117
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-dimethyl, $R^3$ is methoxy and $YR^2$ for each compound corresponds to one row of Table A Table 118
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4,6-trimethyl, $R^3$ is methoxy and $YR^2$ for each compound corresponds to one row of Table A Table 119
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro-4-cyano, $R^3$ is methoxy and $YR^2$ for each compound corresponds to one row of Table A Table 120
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro-4-methyl, $R^3$ is methoxy and $YR^2$ for each compound corresponds to one row of Table A Table 121
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro-4-methoxycarbonyl, $R^3$ is methoxy and $YR^2$ for each compound corresponds to one row of Table A Table 122
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro,4-methoxy, $R^3$ is methoxy and $YR^2$ for each compound corresponds to one row of Table A Table 123
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro,4-methyl, $R^3$ is methoxy and $YR^2$ for each compound corresponds to one row of Table A Table 124
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-methoxycarbonyl, $R^3$ is methoxy and $YR^2$ for each compound corresponds to one row of Table A Table 125
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-methoxy, $R^3$ is methoxy and $YR^2$ for each compound corresponds to one row of Table A Table 126
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-cyano, $R^3$ is methoxy and $YR^2$ for each compound corresponds to one row of Table A Table 127
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro, 4-methoxy, $R^3$ is methoxy and $YR^2$ for each compound corresponds to one row of Table A Table 128
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 3-methyl, $R^3$ is methoxy and $YR^2$ for each compound corresponds to one row of Table A Table 129
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,5-dimethyl, $R^3$ is methoxy and $YR^2$ for each compound corresponds to one row of Table A Table 130
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-cyano, $R^3$ is methoxy and $YR^2$ for each compound corresponds to one row of Table A Table 131
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-bromo, $R^3$ is methoxy and $YR^2$ for each compound corresponds to one row of Table A Table 132
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 5-fluoro, $R^3$ is methoxy and $YR^2$ for each compound corresponds to one row of Table A Table 133
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-methoxy, $R^3$ is methoxy and $YR^2$ for each compound corresponds to one row of Table A Table 134
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-methoxycarbonyl, $R^3$ is methoxy and $YR^2$ for each compound corresponds to one row of Table A Table 135
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,5-dimethyl, 4-bromo, $R^3$ is methoxy and $YR^2$ for each compound corresponds to one row of Table A Table 136
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 4-bromo, $R^3$ is methoxy and $YR^2$ for each compound corresponds to one row of Table A Table 137
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 4-methoxy, $R^3$ is methoxy and $YR^2$ for each compound corresponds to one row of Table A Table 138
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 5-methyl, $R^3$ is methoxy and $YR^2$ for each compound corresponds to one row of Table A Table 139
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is pentafluoro, $R^3$ is methoxy and $YR^2$ for each compound corresponds to one row of Table A Table 140
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 5-fluoro, 4-methoxy, $R^3$ is methoxy and $YR^2$ for each compound corresponds to one row of Table A Table 141
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 5-fluoro, $R^3$ is methoxy and $YR^2$ for each compound corresponds to one row of Table A Table 142
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 6-chloro, $R^3$ is cyano and $YR^2$ for each compound corresponds to one row of Table A Table 143
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro, $R^3$ is cyano and $YR^2$ for each compound corresponds to one row of Table A Table 144
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-dichloro, $R^3$ is cyano and $YR^2$ for each compound corresponds to one row of Table A Table 145
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 6-methyl, $R^3$ is cyano and $YR^2$ for each compound corresponds to one row of Table A Table 146
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4,6-trifluoro, $R^3$ is cyano and $YR^2$ for each compound corresponds to one row of Table A Table 147
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl,4-fluoro, $R^3$ is cyano and $YR^2$ for each compound corresponds to one row of Table A Table 148
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro,4-methoxycarbonyl, $R^3$ is cyano and $YR^2$ for each compound corresponds to one row of Table A Table 149
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 4-CN, $R^3$ is cyano and $YR^2$ for each compound corresponds to one row of Table A Table 150
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4,5-trifluoro, $R^3$ is cyano and $YR^2$ for each compound corresponds to one row of Table A Table 151
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4-dichloro, $R^3$ is cyano and $YR^2$ for each compound corresponds to one row of Table A Table 152
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, $R^3$ is cyano and $YR^2$ for each compound corresponds to one row of Table A Table 153
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, $R^3$ is cyano and $YR^2$ for each compound corresponds to one row of Table A Table 154
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4-difluoro, $R^3$ is cyano and $YR^2$ for each compound corresponds to one row of Table A Table 155
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro-4-chloro, $R^3$ is cyano and $YR^2$ for each compound corresponds to one row of Table A Table 156
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro-4-fluoro, $R^3$ is cyano and $YR^2$ for each compound corresponds to one row of Table A Table 157
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,3-difluoro, $R^3$ is cyano and $YR^2$ for each compound corresponds to one row of Table A Table 158
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,5-difluoro, $R^3$ is cyano and $YR^2$ for each compound corresponds to one row of Table A Table 159
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,3,4-trifluoro, $R^3$ is cyano and $YR^2$ for each compound corresponds to one row of Table A Table 160
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, $R^3$ is cyano and $YR^2$ for each compound corresponds to one row of Table A Table 161
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4-dimethyl, $R^3$ is cyano and $YR^2$ for each compound corresponds to one row of Table A Table 162
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl-4-chloro, $R^3$ is cyano and $YR^2$ for each compound corresponds to one row of Table A Table 163
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro-4-methyl, $R^3$ is cyano and $YR^2$ for each compound corresponds to one row of Table A Table 164
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-dimethyl, $R^3$ is cyano and $YR^2$ for each compound corresponds to one row of Table A Table 165
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,4,6-trimethyl, $R^3$ is cyano and $YR^2$ for each compound corresponds to one row of Table A Table 166
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro-4-cyano, $R^3$ is cyano and $YR^2$ for each compound corresponds to one row of Table A Table 167
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro-4-methyl, $R^3$ is cyano and $YR^2$ for each compound corresponds to one row of Table A Table 168
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro-4-methoxycarbonyl, $R^3$ is cyano and $YR^2$ for each compound corresponds to one row of Table A Table 169
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro,4-methoxy, $R^3$ is cyano and $YR^2$ for each compound corresponds to one row of Table A Table 170
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-methyl, $R^3$ is cyano and $YR^2$ for each compound corresponds to one row of Table A Table 171
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-methoxycarbonyl, $R^3$ is cyano and $YR^2$ for each compound corresponds to one row of Table A Table 172
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-bromo, $R^3$ is cyano and $YR^2$ for each compound corresponds to one row of Table A Table 173
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 4-cyano, $R^3$ is cyano and $YR^2$ for each compound corresponds to one row of Table A Table 174
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,6-difluoro, 4-methoxy, $R^3$ is cyano and $YR^2$ for each compound corresponds to one row of Table A Table 175
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 3-methyl, $R^3$ is cyano and $YR^2$ for each compound corresponds to one row of Table A Table 176
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,5-dimethyl, $R^3$ is cyano and $YR^2$ for each compound corresponds to one row of Table A Table 177
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-cyano, $R^3$ is cyano and $YR^2$ for each compound corresponds to one row of Table A Table 178
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-Methyl, 4-bromo, $R^3$ is cyano and $YR^2$ for each compound corresponds to one row of Table A Table 179
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 5-fluoro, $R^3$ is cyano and $YR^2$ for each compound corresponds to one row of Table A Table 180
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-methoxy, $R^3$ is cyano and $YR^2$ for each compound corresponds to one row of Table A Table 181
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-methyl, 4-methoxycarbonyl, $R^3$ is cyano and $YR^2$ for each compound corresponds to one row of Table A Table 182
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2,5-dimethyl, 4-bromo, $R^3$ is cyano and $YR^2$ for each compound corresponds to one row of Table A Table 183
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 4-bromo, $R^3$ is cyano and $YR^2$ for each compound corresponds to one row of Table A Table 184
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 4-methoxy, $R^3$ is cyano and $YR^2$ for each compound corresponds to one row of Table A Table 185
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-fluoro, 5-methyl, $R^3$ is cyano and $YR^2$ for each compound corresponds to one row of Table A Table 186
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is pentafluoro, $R^3$ is cyano and $YR^2$ for each compound corresponds to one row of Table A Table 187
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 5-fluoro, 4-methoxy, $R^3$ is cyano and $YR^2$ for each compound corresponds to one row of Table A Table 188
Compounds of the formulae Ia, Ib, Ic, Id, Ie, If, Ig, Ih, Ii, Ij, Ik, IL, Im, In, Io, Ip, Iq, Ir, Is, It, Iu, Iv, Iw and Ix in which $L_n$ is 2-chloro, 5-fluoro, $R^3$ is cyano and $YR^2$ for each compound corresponds to one row of Table A

TABLE A

| No. | $R^2$ | Y—$R^2$ / Y [N—$R^1$, CH—$R^1$] |
|---|---|---|
| A-1 | $CH_2CH_3$ | NH |
| A-2 | $CH_2CH_3$ | $NCH_3$ |
| A-3 | $CH_2CH_3$ | $NCH_2CH_3$ |
| A-4 | $CH_2CH_2CH_3$ | NH |
| A-5 | $CH_2CH_2CH_3$ | $NCH_3$ |
| A-6 | $CH_2CH_2CH_3$ | $NCH_2CH_3$ |
| A-7 | $CH_2CH_2CH_3$ | $NCH_2CH_2CH_3$ |
| A-8 | $CH_2CH_2F$ | NH |
| A-9 | $CH_2CH_2F$ | $NCH_3$ |
| A-10 | $CH_2CH_2F$ | $NCH_2CH_3$ |
| A-11 | $CH_2CF_3$ | NH |
| A-12 | $CH_2CF_3$ | $NCH_3$ |
| A-13 | $CH_2CF_3$ | $NCH_2CH_3$ |
| A-14 | $CH_2CF_3$ | $NCH_2CH_2CH_3$ |
| A-15 | $CH_2CCl_3$ | NH |
| A-16 | $CH_2CCl_3$ | $NCH_3$ |
| A-17 | $CH_2CCl_3$ | $NCH_2CH_3$ |
| A-18 | $CH_2CCl_3$ | $NCH_2CH_2CH_3$ |
| A-19 | $CH(CH_3)_2$ | NH |
| A-20 | $CH(CH_3)_2$ | $NCH_3$ |
| A-21 | $CH(CH_3)_2$ | $NCH_2CH_3$ |
| A-22 | $CH(CH_3)_2$ | $NCH_2CH_2CH_3$ |
| A-23 | $CH_2C(CH_3)_3$ | NH |
| A-24 | $CH_2C(CH_3)_3$ | $NCH_3$ |
| A-25 | $CH_2C(CH_3)_3$ | $NCH_2CH_3$ |
| A-26 | $CH_2CH(CH_3)_2$ | NH |
| A-27 | $CH_2CH(CH_3)_2$ | $NCH_3$ |
| A-28 | $CH_2CH(CH_3)_2$ | $NCH_2CH_3$ |
| A-29 | (±) $CH(CH_2CH_3)CH_3$ | NH |
| A-30 | (±) $CH(CH_2CH_3)CH_3$ | $NCH_3$ |
| A-31 | (±) $CH(CH_2CH_3)CH_3$ | $NCH_2CH_3$ |
| A-32 | (R) $CH(CH_2CH_3)CH_3$ | NH |
| A-33 | (R) $CH(CH_2CH_3)CH_3$ | $NCH_3$ |
| A-34 | (R) $CH(CH_2CH_3)CH_3$ | $NCH_2CH_3$ |
| A-35 | (S) $CH(CH_2CH_3)CH_3$ | NH |
| A-36 | (S) $CH(CH_2CH_3)CH_3$ | $NCH_3$ |
| A-37 | (S) $CH(CH_2CH_3)CH_3$ | $NCH_2CH_3$ |
| A-38 | (±) $CH(CH_3)$—$CH(CH_3)_2$ | NH |
| A-39 | (±) $CH(CH_3)$—$CH(CH_3)_2$ | $NCH_3$ |
| A-40 | (±) $CH(CH_3)$—$CH(CH_3)_2$ | $NCH_2CH_3$ |
| A-41 | (R) $CH(CH_3)$—$CH(CH_3)_2$ | NH |
| A-42 | (R) $CH(CH_3)$—$CH(CH_3)_2$ | $NCH_3$ |
| A-43 | (R) $CH(CH_3)$—$CH(CH_3)_2$ | $NCH_2CH_3$ |
| A-44 | (S) $CH(CH_3)$—$CH(CH_3)_2$ | NH |
| A-45 | (S) $CH(CH_3)$—$CH(CH_3)_2$ | $NCH_3$ |
| A-46 | (S) $CH(CH_3)$—$CH(CH_3)_2$ | $NCH_2CH_3$ |
| A-47 | (±) $CH(CH_3)$—$C(CH_3)_3$ | NH |
| A-48 | (±) $CH(CH_3)$—$C(CH_3)_3$ | $NCH_3$ |
| A-49 | (±) $CH(CH_3)$—$C(CH_3)_3$ | $NCH_2CH_3$ |
| A-50 | (R) $CH(CH_3)$—$C(CH_3)_3$ | NH |
| A-51 | (R) $CH(CH_3)$—$C(CH_3)_3$ | $NCH_3$ |
| A-52 | (R) $CH(CH_3)$—$C(CH_3)_3$ | $NCH_2CH_3$ |
| A-53 | (S) $CH(CH_3)$—$C(CH_3)_3$ | NH |
| A-54 | (S) $CH(CH_3)$—$C(CH_3)_3$ | $NCH_3$ |
| A-55 | (S) $CH(CH_3)$—$C(CH_3)_3$ | $NCH_2CH_3$ |
| A-56 | (±) $CH(CH_3)$—$CF_3$ | NH |
| A-57 | (±) $CH(CH_3)$—$CF_3$ | $NCH_3$ |
| A-58 | (±) $CH(CH_3)$—$CF_3$ | $NCH_2CH_3$ |
| A-59 | (R) $CH(CH_3)$—$CF_3$ | NH |
| A-60 | (R) $CH(CH_3)$—$CF_3$ | $NCH_3$ |
| A-61 | (R) $CH(CH_3)$—$CF_3$ | $NCH_2CH_3$ |

TABLE A-continued

| No. | R² | Y [N—R¹, CH—R¹] |
|---|---|---|
| A-62 | (S) CH(CH₃)—CF₃ | NH |
| A-63 | (S) CH(CH₃)—CF₃ | NCH₃ |
| A-64 | (S) CH(CH₃)—CF₃ | NCH₂CH₃ |
| A-65 | (±) CH(CH₃)—CCl₃ | NH |
| A-66 | (±) CH(CH₃)—CCl₃ | CH₃ |
| A-67 | (±) CH(CH₃)—CCl₃ | NCH₂CH₃ |
| A-68 | (R) CH(CH₃)—CCl₃ | NH |
| A-69 | (R) CH(CH₃)—CCl₃ | NCH₃ |
| A-70 | (R) CH(CH₃)—CCl₃ | NCH₂CH₃ |
| A-71 | (S) CH(CH₃)—CCl₃ | NH |
| A-72 | (S) CH(CH₃)—CCl₃ | NCH₃ |
| A-73 | (S) CH(CH₃)—CCl₃ | NCH₂CH₃ |
| A-74 | CH₂C(CH₃)=CH₂ | NH |
| A-75 | CH₂C(CH₃)=CH₂ | NCH₃ |
| A-76 | CH₂C(CH₃)=CH₂ | NCH₂CH₃ |
| A-77 | CH(CH₃)₂₃ | O |
| A-78 | CH(CH₃)₂₃ | S |
| A-79 | CH₂CH(CH₃)₂ | O |
| A-80 | CH₂CH(CH₃)₂ | S |
| A-81 | CH₂C(CH₃)₃ | O |
| A-82 | CH₂C(CH₃)₃ | S |
| A-83 | CH(CH₂CH₃)CH₃ | O |
| A-84 | CH(CH₂CH₃)CH₃ | S |
| A-85 | CH(CH₃)—CH(CH₃)₂ | O |
| A-86 | CH(CH₃)—CH(CH₃)₂ | S |
| A-87 | CH(CH₃)—C(CH₃)₃ | O |
| A-88 | CH(CH₃)—C(CH₃)₃ | S |
| A-89 | CH(CH₃)—CF₃ | O |
| A-90 | CH(CH₃)—CF₃ | S |
| A-91 | CH(CH₃)—CCl₃ | O |
| A-92 | CH(CH₃)—CCl₃ | S |
| A-93 | CH₂C(CH₃)=CH₂ | O |
| A-94 | CH₂C(CH₃)=CH₂ | S |
| A-95 | cyclopentyl | NH |
| A-96 | cyclopentyl | NCH₃ |
| A-97 | cyclopentyl | NCH₂CH₃ |
| A-98 | cyclohexyl | NH |
| A-99 | cyclohexyl | NCH₃ |
| A-100 | cyclohexyl | NCH₂CH₃ |
| A-101 | 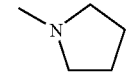 | |
| A-102 | 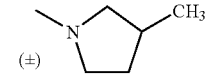 (±) | |
| A-103 | 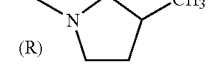 (R) | |
| A-104 | 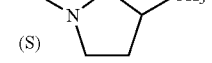 (S) | |
| A-105 | 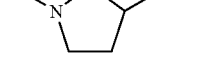 | |
| A-106 | 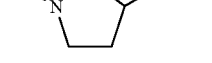 | |
| A-107 | 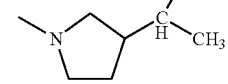 | |
| A-108 | 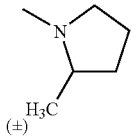 (±) | |
| A-109 | 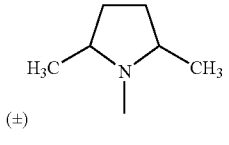 (±) | |
| A-110 | 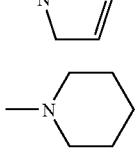 | |
| A-111 | 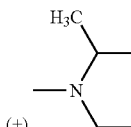 | |
| A-112 | 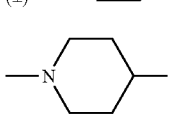 (±) | |
| A-113 | 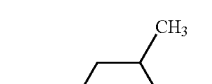 | |
| A-114 | 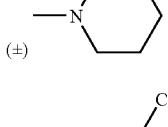 (±) | |
| A-115 | 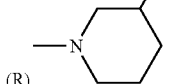 (R) | |
| A-116 | 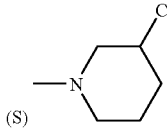 (S) | |
| A-117 |  | |
| A-118 | 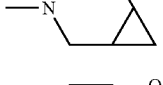 | |
| A-119 | 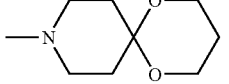 | |

TABLE A-continued

| No. | R² | Y [N—R¹, CH—R¹] |
|---|---|---|
| A-120 | —N(piperidinyl-like ring) | |
| A-121 | $CH_3$ | |
| A-122 | $CH_2CH_3$ | |
| A-123 | $CH_2CH_2CH_3$ | |
| A-124 | $CH(CH_3)_2$ | |
| A-125 | $CH_2CH(CH_3)_2$ | |
| A-126 | (±) $CH(CH_3)CH_2CH_3$ | |
| A-127 | (R) $CH(CH_3)CH_2CH_3$ | |
| A-128 | (S) $CH(CH_3)CH_2CH_3$ | |
| A-129 | $(CH_2)_3CH_3$ | |
| A-130 | $C(CH_3)_3$ | |
| A-131 | $(CH_2)_4CH_3$ | |
| A-132 | $CH(CH_2CH_3)_2$ | |
| A-133 | $CH_2CH_2CH(CH_3)_2$ | |
| A-134 | (±) $CH(CH_3)(CH_2)_2CH_3$ | |
| A-135 | (R) $CH(CH_3)(CH_2)_2CH_3$ | |
| A-136 | (S) $CH(CH_3)(CH_2)_2CH_3$ | |
| A-137 | (±) $CH_2CH(CH_3)CH_2CH_3$ | |
| A-138 | (R) $CH_2CH(CH_3)CH_2CH_3$ | |
| A-139 | (S) $CH_2CH(CH_3)CH_2CH_3$ | |
| A-140 | (±) $CH(CH_3)CH(CH_3)_2$ | |
| A-141 | (R) $CH(CH_3)CH(CH_3)_2$ | |
| A-142 | (S) $CH(CH_3)CH(CH_3)_2$ | |
| A-143 | $(CH_2)_5CH_3$ | |
| A-144 | (±,±) $CH(CH_3)CH(CH_3)CH_2CH_3$ | |
| A-145 | (±,R) $CH(CH_3)CH(CH_3)CH_2CH_3$ | |
| A-146 | (±,S) $CH(CH_3)CH(CH_3)CH_2CH_3$ | |
| A-147 | (±) $CH_2CH(CH_3)CF_3$ | |
| A-148 | (R) $CH_2CH(CH_3)CF_3$ | |
| A-149 | (S) $CH_2CH(CH_3)CF_3$ | |
| A-150 | (±) $CH_2CH(CF_3)CH_2CH_3$ | |
| A-151 | (R) $CH_2CH(CF_3)CH_2CH_3$ | |
| A-152 | (S) $CH_2CH(CF_3)CH_2CH_3$ | |
| A-153 | (±,±) $CH(CH_3)CH(CH_3)CF_3$ | |
| A-154 | (±,R) $CH(CH_3)CH(CH_3)CF_3$ | |
| A-155 | (±,S) $CH(CH_3)CH(CH_3)CF_3$ | |
| A-156 | (±,±) $CH(CH_3)CH(CF_3)CH_2CH_3$ | |
| A-157 | (±,R) $CH(CH_3)CH(CF_3)CH_2CH_3$ | |
| A-158 | (±,S) $CH(CH_3)CH(CF_3)CH_2CH_3$ | |
| A-159 | $CF_3$ | |
| A-160 | $CF_2CF_3$ | |
| A-161 | $CF_2CF_2CF_3$ | |
| A-162 | $c-C_3H_5$ | |
| A-163 | $(1-CH_3)-c-C_3H_4$ | |
| A-164 | $c-C_5H_9$ | |
| A-165 | $c-C_6H_{11}$ | |
| A-166 | $(4-CH_3)-c-C_6H_{10}$ | |
| A-167 | $CH_2C(CH_3)=CH_2$ | |
| A-168 | $CH_2CH_2C(CH_3)=CH_2$ | |
| A-169 | $CH_2-C(CH_3)_3$ | |
| A-170 | $CH_2-Si(CH_3)_3$ | |
| A-171 | $n-C_6H_{13}$ | |
| A-172 | $(CH_2)_3-CH(CH_3)_2$ | |
| A-173 | $(CH_2)_2-CH(CH_3)-C_2H_5$ | |
| A-174 | $CH_2-CH(CH_3)-n-C_3H_7$ | |
| A-175 | $CH(CH_3)-n-C_4H_9$ | |
| A-176 | $CH_2-CH(C_2H_5)_2$ | |
| A-177 | $CH(C_2H_5)-n-C_3H_7$ | |
| A-178 | $CH_2-c-C_5H_9$ | |
| A-179 | $CH_2-CH(CH_3)-CH(CH_3)_2$ | |
| A-180 | $CH(CH_3)-CH_2CH(CH_3)_2$ | |
| A-181 | $CH(CH_3)-CH(CH_3)-C_2H_5$ | |
| A-182 | $CH(CH_3)-C(CH_3)_3$ | |
| A-183 | $(CH_2)_2-C(CH_3)_3$ | |
| A-184 | $CH_2-C(CH_3)_2-C_2H_5$ | |
| A-185 | $2-CH_3-c-C_5H_8$ | |
| A-186 | $3-CH_3-c-C_5H_8$ | |
| A-187 | $C(CH_3)_2-n-C_3H_7$ | |
| A-188 | $(CH_2)_6-CH_3$ | |
| A-189 | $(CH_2)_4-CH(CH_3)_2$ | |
| A-190 | $(CH_2)_3-CH(CH_3)-C_2H_5$ | |
| A-191 | $(CH_2)_2-CH(CH_3)-n-C_3H_7$ | |
| A-192 | $CH_2-CH(CH_3)-n-C_4H_9$ | |
| A-193 | $CH(CH_3)-n-C_5H_{11}$ | |
| A-194 | $(CH_2)_3C(CH_3)_3$ | |
| A-195 | $(CH_2)_2CH(CH_3)-CH(CH_3)_2$ | |
| A-196 | $(CH_2)CH(CH_3)-CH_2CH(CH_3)_2$ | |
| A-197 | $CH(CH_3)(CH_2)_2-CH(CH_3)_2$ | |
| A-198 | $(CH_2)_2C(CH_3)_2C_2H_5$ | |
| A-199 | $CH_2CH(CH_3)CH(CH_3)C_2H_5$ | |
| A-200 | $CH(CH_3)CH_2CH(CH_3)C_2H_5$ | |
| A-201 | $CH_2C(CH_3)_2-n-C_3H_7$ | |
| A-202 | $CH(CH_3)CH(CH_3)-n-C_3H_7$ | |
| A-203 | $C(CH_3)_2-n-C_4H_9$ | |
| A-204 | $(CH_2)_2CH(C_2H_5)_2$ | |
| A-205 | $CH_2CH(C_2H_5)-n-C_3H_7$ | |
| A-206 | $CH(C_2H_5)-n-C_4H_9$ | |
| A-207 | $CH_2CH(CH_3)C(CH_3)_3$ | |
| A-208 | $CH(CH_3)CH_2C(CH_3)_3$ | |
| A-209 | $CH_2C(CH_3)_2CH(CH_3)_2$ | |
| A-210 | $CH_2CH(C_2H_5)CH(CH_3)_2$ | |
| A-211 | $CH(CH_3)CH(CH_3)CH(CH_3)_2$ | |
| A-212 | $C(CH_3)_2CH_2CH(CH_3)_2$ | |
| A-213 | $CH(C_2H_5)CH_2CH(CH_3)_2$ | |
| A-214 | $CH(CH_3)C(CH_3)_2C_2H_5$ | |
| A-215 | $CH(CH_3)CH(C_2H_5)_2$ | |
| A-216 | $C(CH_3)_2CH(CH_3)C_2H_5$ | |
| A-217 | $CH(C_2H_5)CH(CH_3)C_2H_5$ | |
| A-218 | $C(CH_3)(C_2H_5)-n-C_3H_7$ | |
| A-219 | $CH(n-C_3H_7)_2$ | |
| A-220 | $CH(n-C_3H_7)CH(CH_3)_2$ | |
| A-221 | $C(CH_3)_2C(CH_3)_3$ | |
| A-222 | $C(CH_3)(C_2H_5)-CH(CH_3)_2$ | |
| A-223 | $C(C_2H_5)_3$ | |
| A-224 | $(3-CH_3)-c-C_6H_{10}$ | |
| A-225 | $(2-CH_3)-c-C_6H_{10}$ | |
| A-226 | $n-C_8H_{17}$ | |
| A-227 | $CH_2C(=NO—CH_3)CH_3$ | |
| A-228 | $CH_2C(=NO—C_2H_5)CH_3$ | |
| A-229 | $CH_2C(=NO-n-C_3H_7)CH_3$ | |
| A-230 | $CH_2C(=NO-i-C_3H_7)CH_3$ | |
| A-231 | $CH(CH_3)C(=NOCH_3)CH_3$ | |
| A-232 | $CH(CH_3)C(=NOC_2H_5)CH_3$ | |
| A-233 | $CH(CH_3)C(=NO-n-C_3H_7)CH_3$ | |
| A-234 | $CH(CH_3)C(=NO-i-C_3H_7)CH_3$ | |
| A-235 | $C(=NOCH_3)C(=NOCH_3)CH_3$ | |
| A-236 | $C(=NOCH_3)C(=NOC_2H_5)CH_3$ | |
| A-237 | $C(=NOCH_3)C(=NO-n-C_3H_7)CH_3$ | |
| A-238 | $C(=NOCH_3)C(=NO-i-C_3H_7)CH_3$ | |
| A-239 | $C(=NOC_2H_5)C(=NOCH_3)CH_3$ | |
| A-240 | $C(=NOC_2H_5)C(=NOC_2H_5)CH_3$ | |
| A-241 | $C(=NOC_2H_5)C(=NO-n-C_3H_7)CH_3$ | |
| A-242 | $C(=NOC_2H_5)C(=NO-i-C_3H_7)CH_3$ | |
| A-243 | $CH_2C(=NO—CH_3)C_2H_5$ | |
| A-244 | $CH_2C(=NO—C_2H_5)C_2H_5$ | |
| A-245 | $CH_2C(=NO-n-C_3H_7)C_2H_5$ | |
| A-246 | $CH_2C(=NO-i-C_3H_7)C_2H_5$ | |
| A-247 | $CH(CH_3)C(=NOCH_3)C_2H_5$ | |
| A-248 | $CH(CH_3)C(=NOC_2H_5)C_2H_5$ | |
| A-249 | $CH(CH_3)C(=NO-n-C_3H_7)C_2H_5$ | |
| A-250 | $CH(CH_3)C(=NO-n-C_3H_7)C_2H_5$ | |
| A-251 | $C(=NOCH_3)C(=NOCH_3)C_2H_5$ | |
| A-252 | $C(=NOCH_3)C(=NOC_2H_5)C_2H_5$ | |
| A-253 | $C(NOCH_3)C(=NO-n-C_3H_7)C_2H_5$ | |
| A-254 | $C(=NOCH_3)C(=NO-i-C_3H_7)C_2H_5$ | |
| A-255 | $C(=NOC_2H_5)C(=NOCH_3)C_2H_5$ | |
| A-256 | $C(=NOC_2H_5)C(=NOC_2H_5)C_2H_5$ | |
| A-257 | $C(=NOC_2H_5)C(=NO-n-C_3H_7)C_2H_5$ | |
| A-258 | $C(=NOC_2H_5)C(=NO-i-C_3H_7)C_2H_5$ | |
| A-259 | $CH=CH—CH_2CH_3$ | |
| A-260 | $CH_2—CH=CH—CH_3$ | |
| A-261 | $CH_2—CH_2—CH=CH_2$ | |
| A-262 | $C(CH_3)_2CH_2CH_3$ | |
| A-263 | $CH=C(CH_3)_2$ | |
| A-264 | $C(=CH_2)—CH_2CH_3$ | |
| A-265 | $C(CH_3)=CH—CH_3$ | |

TABLE A-continued

| No. | R² | Y [N—R¹, CH—R¹] |
|---|---|---|
| A-266 | CH(CH₃)CH=CH₂ | |
| A-267 | CH=CH-n-C₃H₇ | |
| A-268 | CH₂—CH=CH—C₂H₅ | |
| A-269 | (CH₂)₂—CH=CH—CH₃ | |
| A-270 | (CH₂)₃—CH=CH₂ | |
| A-271 | CH=CH—CH(CH₃)₂ | |
| A-272 | CH₂—CH=C(CH₃)₂ | |
| A-273 | (CH₂)₂—C(=CH₂)—CH₃ | |
| A-274 | CH=C(CH₃)—C₂H₅ | |
| A-275 | CH₂—C(=CH₂)—C₂H₅ | |
| A-276 | CH₂—C(CH₃)=CH—CH₃ | |
| A-277 | CH₂—CH(CH₃)—CH=CH₂ | |
| A-278 | C(=CH₂)—CH₂—CH₂—CH₃ | |
| A-279 | C(CH₃)=CH—CH₂—CH₃ | |
| A-280 | CH(CH₃)—CH=CH—CH₃ | |
| A-281 | CH(CH₃)—CH₂—CH=CH₂ | |
| A-282 | C(=CH₂)CH(CH₃)₂ | |
| A-283 | C(CH₃)=C(CH₃)₂ | |
| A-284 | CH(CH₃)—C(=CH₂)—CH₃ | |
| A-285 | C(CH₃)₂—CH=CH₂ | |
| A-286 | C(C₂H₅)=CH—CH₃ | |
| A-287 | CH(C₂H₅)—CH=CH₂ | |
| A-288 | CH=CH—CH₂—CH₂—CH₂—CH₃ | |
| A-289 | CH₂—CH=CH—CH₂—CH₂—CH₃ | |
| A-290 | CH₂—CH₂—CH=CH—CH₂—CH₃ | |
| A-291 | CH₂—CH₂—CH₂—CH=CH—CH₃ | |
| A-292 | CH₂—CH₂—CH₂—CH₂—CH=CH₂ | |
| A-293 | CH=CH—CH₂—CH(CH₃)CH₃ | |
| A-294 | CH₂—CH=CH—CH(CH₃)CH₃ | |
| A-295 | CH₂—CH₂—CH=C(CH₃)CH₃ | |
| A-296 | CH₂—CH₂—CH₂—C(CH₃)=CH₂ | |
| A-297 | CH=CH—CH(CH₃)—CH₂—CH₃ | |
| A-298 | CH₂—CH=C(CH₃)—CH₂—CH₃ | |
| A-299 | CH₂—CH₂—C(=CH₂)—CH₂—CH₃ | |
| A-300 | CH₂—CH₂—C(CH₃)=CH—CH₃ | |
| A-301 | CH₂—CH₂—CH(CH₃)—CH=CH₂ | |
| A-302 | CH=C(CH₃)—CH₂—CH₂—CH₃ | |
| A-303 | CH₂—C(=CH₂)—CH₂—CH₂—CH₃ | |
| A-304 | CH₂—C(CH₃)=CH—CH₂—CH₃ | |
| A-305 | CH₂—CH(CH₃)—CH=CH—CH₃ | |
| A-306 | CH₂—CH(CH₃)—CH₂—CH=CH₂ | |
| A-307 | C(=CH₂)—CH₂—CH₂—CH₂—CH₃ | |
| A-308 | C(CH₃)=CH—CH₂—CH₂—CH₃ | |
| A-309 | CH(CH₃)—CH=CH—CH₂—CH₃ | |
| A-310 | CH(CH₃)—CH₂—CH=CH—CH₃ | |
| A-311 | CH(CH₃)—CH₂—CH₂—CH=CH₂ | |
| A-312 | CH=CH—C(CH₃)₃ | |
| A-313 | CH=C(CH₃)—CH(CH₃)—CH₃ | |
| A-314 | CH₂—C(=CH₂)—CH(CH₃)—CH₃ | |
| A-315 | CH₂—C(CH₃)₂—CH=CH₂ | |
| A-316 | CH₂—CH(CH₃)—C(=CH₂)—CH₃ | |
| A-317 | C(=CH₂)—CH₂—CH(CH₃)—CH₃ | |
| A-318 | C(CH₃)=CH—CH(CH₃)—CH₃ | |
| A-319 | CH(CH₃)—CH=C(CH₃)—CH₃ | |
| A-320 | CH(CH₃)—CH₂—C(=CH₂)—CH₃ | |
| A-321 | CH=C(CH₂—CH₃)—CH₂—CH₃ | |
| A-322 | CH₂—C(=CH—CH₃)—CH₂—CH₃ | |
| A-323 | CH₂—CH(CH=CH₂)—CH₂—CH₃ | |
| A-324 | C(=CH—CH₃)—CH₂—CH₂—CH₃ | |
| A-325 | CH(CH=CH₂)—CH₂—CH₂—CH₃ | |
| A-326 | C(CH₂—CH₃)=CH—CH₂—CH₃ | |
| A-327 | CH(CH₂—CH₃)—CH=CH—CH₃ | |
| A-328 | CH(CH₂—CH₃)—CH₂—CH=CH₂ | |
| A-329 | CH₂—C(CH₃)₂—CH=CH₂ | |
| A-330 | C(=CH₂)—CH(CH₃)—CH₂—CH₃ | |
| A-331 | C(CH₃)₂—CH₂—CH=CH₂ | |
| A-332 | CH(CH₃)—C(=CH₂)—CH₂—CH₃ | |
| A-333 | CH(CH₃)—C(CH₃)=CH—CH₃ | |
| A-334 | CH(CH₃)—CH(CH₃)—CH=CH₂ | |
| A-335 | C(CH₃)₂—CH=CH—CH₃ | |
| A-336 | C(CH₃)₂—CH₂—CH=CH₂ | |
| A-337 | C(=CH₂)—C(CH₃)₃ | |
| A-338 | C(=CH—CH₃)—CH(CH₃)—CH₃ | |
| A-339 | CH(CH=CH₂)—CH(CH₃)—CH₃ | |
| A-340 | C(CH₂—CH₃)=C(CH₃)—CH₃ | |
| A-341 | CH(CH₂—CH₃)—C(=CH₂)—CH₃ | |
| A-342 | C(CH₃)₂—C(=CH₂)—CH₃ | |
| A-343 | C(CH₃)(CH=CH₂)—CH₂—CH₃ | |
| A-344 | C(CH₃)(CH₂CH₃)—CH₂—CH₂—CH₃ | |
| A-345 | CH(CH₂CH₃)—CH(CH₃)—CH₂—CH₃ | |
| A-346 | CH(CH₂CH₃)—CH₂—CH(CH₃)—CH₃ | |
| A-347 | C(CH₃)₂—C(CH₃)₃ | |
| A-348 | C(CH₃)₂—C(CH₃)₃ | |
| A-349 | C(CH₃)(CH₂—CH₃)—CH(CH₃)₂ | |
| A-350 | CH(CH(CH₃)₂)—CH(CH₃)₂ | |
| A-351 | CH=CH—CH₂—CH₂—CH₂—CH₂—CH₃ | |
| A-352 | CH₂—CH=CH—CH₂—CH₂—CH₂—CH₃ | |
| A-353 | CH₂—CH₂—CH=CH—CH₂—CH₂—CH₃ | |
| A-354 | CH₂—CH₂—CH₂—CH=CH—CH₂—CH₃ | |
| A-355 | CH₂—CH₂—CH₂—CH₂—CH=CH—CH₃ | |
| A-356 | CH₂—CH₂—CH₂—CH₂—CH₂—CH=CH₂ | |
| A-357 | CH=CH—CH₂—CH₂—CH(CH₃)—CH₃ | |
| A-358 | CH₂—CH=CH—CH₂—CH(CH₃)—CH₃ | |
| A-359 | CH₂—CH₂—CH=CH—CH(CH₃)—CH₃ | |
| A-360 | CH₂—CH₂—CH₂—CH=C(CH₃)—CH₃ | |
| A-361 | CH₂—CH₂—CH₂—CH₂—C(=CH₂)—CH₃ | |
| A-362 | CH=CH—CH₂—CH(CH₃)—CH₂—CH₃ | |
| A-363 | CH₂—CH=CH—CH(CH₃)—CH₂—CH₃ | |
| A-364 | CH₂—CH₂—CH=C(CH₃)—CH₂—CH₃ | |
| A-365 | CH₂—CH₂—CH₂—C(=CH₂)—CH₂—CH₃ | |
| A-366 | CH₂—CH₂—CH₂—C(CH₃)=CH—CH₃ | |
| A-367 | CH₂—CH₂—CH₂—CH(CH₃)—CH=CH₂ | |
| A-368 | CH=CH—CH(CH₃)—CH₂—CH₂—CH₃ | |
| A-369 | CH₂—CH(CH₃)—CH₂—CH₂—CH₃ | |
| A-370 | CH₂—CH₂—C(=CH₂)—CH₂—CH₂—CH₃ | |
| A-371 | CH₂—CH₂—C(CH₃)=CH—CH₂—CH₃ | |
| A-372 | CH₂—CH₂—CH(CH₃)—CH=CH—CH₃ | |
| A-373 | CH₂—CH₂—CH(CH₃)—CH₂—CH=CH₂ | |
| A-374 | CH=C(CH₃)—CH₂—CH₂—CH₂—CH₃ | |
| A-375 | CH₂—C(=CH₂)—CH₂—CH₂—CH₂—CH₃ | |
| A-376 | CH₂—C(CH₃)=CH—CH₂—CH₂—CH₃ | |
| A-377 | CH₂—CH(CH₃)—CH=CH—CH₂—CH₃ | |
| A-378 | CH₂—CH(CH₃)—CH₂—CH=CH—CH₃ | |
| A-379 | CH₂—CH(CH₃)—CH₂—CH₂—CH=CH₂ | |
| A-380 | C(=CH₂)—CH₂—CH₂—CH₂—CH₂—CH₃ | |
| A-381 | C(CH₃)=CH—CH₂—CH₂—CH₂—CH₃ | |
| A-382 | CH(CH₃)—CH=CH—CH₂—CH₂—CH₃ | |
| A-383 | CH(CH₃)—CH₂—CH=CH—CH₂—CH₃ | |
| A-384 | CH(CH₃)—CH₂—CH₂—CH=CH—CH₃ | |
| A-385 | CH(CH₃)—CH₂—CH₂—CH₂—CH=CH₂ | |
| A-386 | CH=CH—CH₂—C(CH₃)₃ | |
| A-387 | CH₂—CH=CH—C(CH₃)₃ | |
| A-388 | CH=CH—CH(CH₃)—CH(CH₃)₂ | |
| A-389 | CH₂—CH=C(CH₃)—CH(CH₃)₂ | |
| A-390 | CH₂—CH₂—C(=CH₂)—CH(CH₃)₂ | |
| A-391 | CH₂—CH₂—C(CH₃)=C(CH₃)₂ | |
| A-392 | CH₂—CH₂—CH(CH₃)—C(=CH₂)—CH₃ | |
| A-393 | CH=C(CH₃)—CH₂—CH(CH₃)₂ | |
| A-394 | CH₂—C(=CH₂)—CH₂—CH(CH₃)₂ | |
| A-395 | CH₂—C(CH₃)=CH—CH(CH₃)₂ | |
| A-396 | CH₂—CH(CH₃)—CH=C(CH₃)₂ | |
| A-397 | CH₂—CH(CH₃)—CH₂—C(=CH₂)—CH₃ | |
| A-398 | C(=CH₂)—CH₂—CH₂—CH(CH₃)₂ | |
| A-399 | C(CH₃)=CH—CH₂—CH(CH₃)₂ | |
| A-400 | CH(CH₃)—CH=CH—CH(CH₃)₂ | |
| A-401 | CH(CH₃)—CH₂—CH=C(CH₃)₂ | |
| A-402 | CH(CH₃)—CH₂—C(=CH₂)—CH₂—CH₃ | |
| A-403 | CH=CH—C(CH₃)₂—CH₂—CH₃ | |
| A-404 | CH₂—CH₂—C(CH₃)₂—CH=CH₂ | |
| A-405 | CH=C(CH₃)—CH(CH₃)—CH₂—CH₃ | |
| A-406 | CH₂—C(=CH₂)—CH(CH₃)—CH₂—CH₃ | |
| A-407 | CH₂—C(CH₃)=C(CH₃)—CH₂—CH₃ | |
| A-408 | CH₂—CH(CH₃)—C(=CH₂)—CH₂—CH₃ | |
| A-409 | CH₂—CH(CH₃)—C(CH₃)=CH—CH₃ | |
| A-410 | CH₂—CH(CH₃)—CH(CH₃)—CH=CH₂ | |
| A-411 | C(=CH₂)—CH(CH₃)—CH₂—CH₂—CH₃ | |
| A-412 | C(CH₃)=CH—CH(CH₃)—CH₂—CH₃ | |
| A-413 | CH(CH₃)—CH=C(CH₃)—CH₂—CH₃ | |
| A-414 | CH(CH₃)—CH₂—C(=CH₂)—CH₂—CH₃ | |
| A-415 | CH(CH₃)—CH₂—C(CH₃)=CH—CH₃ | |

TABLE A-continued

| No. | R² | Y [N—R¹, CH—R¹] |
|---|---|---|
| A-416 | CH(CH₃)—CH₂—CH(CH₃)—CH=CH₂ | |
| A-417 | CH₂—C(CH₃)₂—CH=CH—CH₃ | |
| A-418 | CH₂—C(CH₃)₂—CH₂—CH=CH₂ | |
| A-419 | C(=CH₂)—CH(CH₃)—CH₂—CH₂—CH₃ | |
| A-420 | C(CH₃)=C(CH₃)—CH₂—CH₂—CH₃ | |
| A-421 | CH(CH₃)—C(=CH₂)—CH₂—CH₂—CH₃ | |
| A-422 | CH(CH₃)—C(CH₃)=CH—CH₂—CH₃ | |
| A-423 | CH(CH₃)—CH(CH₃)—CH=CH—CH₃ | |
| A-424 | CH(CH₃)—CH(CH₃)—CH₂—CH=CH₂ | |
| A-425 | C(CH₃)₂—CH=CH—CH₂—CH₃ | |
| A-426 | C(CH₃)₂—CH₂—CH=CH—CH₃ | |
| A-427 | C(CH₃)₂—CH₂—CH₂—CH=CH₂ | |
| A-428 | CH=CH—CH(CH₂—CH₃)—CH₂—CH₃ | |
| A-429 | CH₂—CH=C(CH₂—CH₃)—CH₂—CH₃ | |
| A-430 | CH₂—CH₂—C(=CH—CH₃)—CH₂—CH₃ | |
| A-431 | CH₂—CH₂—CH(CH=CH₂)—CH₂—CH₃ | |
| A-432 | CH=C(CH₂—CH₃)—CH₂—CH₂—CH₃ | |
| A-433 | CH₂—C(=CH—CH₃)—CH₂—CH₂—CH₃ | |
| A-434 | CH₂—CH(CH=CH₂)—CH₂—CH₂—CH₃ | |
| A-435 | CH₂—C(CH₂—CH₃)=CH—CH₂—CH₃ | |
| A-436 | CH₂—CH(CH₂—CH₃)—CH=CH—CH₃ | |
| A-437 | CH₂—CH(CH₂—CH₃)—CH₂—CH=CH₂ | |
| A-438 | C(=CH—CH₃)—CH₂—CH₂—CH₂—CH₃ | |
| A-439 | CH(CH=CH₂)—CH₂—CH₂—CH₂—CH₃ | |
| A-440 | C(CH₂—CH₃)=CH—CH₂—CH₂—CH₃ | |
| A-441 | CH(CH₂—CH₃)—CH=CH—CH₂—CH₃ | |
| A-442 | CH(CH₂—CH₃)—CH₂—CH=CH—CH₃ | |
| A-443 | CH(CH₂—CH₃)—CH₂—CH₂—CH=CH₂ | |
| A-444 | C(=CH—CH₂—CH₃)—CH₂—CH₂—CH₃ | |
| A-445 | C(CH=CH—CH₃)—CH₂—CH₂—CH₃ | |
| A-446 | C(CH₂—CH=CH₂)—CH₂—CH₂—CH₃ | |
| A-447 | CH=C(CH₃)—C(CH₃)₃ | |
| A-448 | CH₂—C(=CH₂)—C(CH₃)₃ | |
| A-449 | CH₂—C(CH₃)₂—CH(=CH₂)—CH₃ | |
| A-450 | C(=CH₂)—CH(CH₃)—CH(CH₃)—CH₃ | |
| A-451 | C(CH₃)=C(CH₃)—CH(CH₃)—CH₃ | |
| A-452 | CH(CH₃)—C(=CH₂)—CH(CH₃)—CH₃ | |
| A-453 | CH(CH₃)—C(CH₃)=C(CH₃)—CH₃ | |
| A-454 | CH(CH₃)—CH(CH₃)—C(=CH₂)—CH₃ | |
| A-455 | C(CH₃)₂—CH=C(CH₃)—CH₃ | |
| A-456 | C(CH₃)₂—CH₂—C(=CH₂)—CH₃ | |
| A-457 | C(CH₃)₂—C(=CH₂)—CH₂—CH₃ | |
| A-458 | C(CH₃)₂—C(CH₃)=CH—CH₃ | |
| A-459 | C(CH₃)₂—CH(CH₃)CH=CH₂ | |
| A-460 | CH(CH₂—CH₃)—CH₂—CH(CH₃)—CH₃ | |
| A-461 | CH(CH₂—CH₃)—CH(CH₃)—CH₂—CH₃ | |
| A-462 | C(CH₃)(CH₂—CH₃)—CH₂—CH₂—CH₃ | |
| A-463 | CH(i-C₃H₇)—CH₂—CH₂—CH₃ | |
| A-464 | CH=C(CH₂—CH₃)—CH(CH₃)—CH₃ | |
| A-465 | CH₂—C(=CH—CH₃)—CH(CH₃)—CH₃ | |
| A-466 | CH₂—CH(CH=CH₂)—CH(CH₃)—CH₃ | |
| A-467 | CH₂—C(CH₂—CH₃)=C(CH₃)—CH₃ | |
| A-468 | CH₂—CH(CH₂—CH₃)—C(=CH₂)—CH₃ | |
| A-469 | CH₂—C(CH₃)(CH=CH₂)—CH₂—CH₃ | |
| A-470 | C(=CH₂)—CH(CH₂—CH₃)—CH₂—CH₃ | |
| A-471 | C(CH₃)=C(CH₂—CH₃)—CH₂—CH₃ | |
| A-472 | CH(CH₃)—C(=CH—CH₃)—CH₂—CH₃ | |
| A-473 | CH(CH₃)—CH(CH=CH₂)—CH₂—CH₃ | |
| A-474 | CH=C(CH₂—CH₃)—CH(CH₃)—CH₃ | |
| A-475 | CH₂—C(=CH—CH₃)—CH(CH₃)—CH₃ | |
| A-476 | CH₂—CH(CH=CH₂)—CH(CH₃)—CH₃ | |
| A-477 | CH₂—C(CH₂—CH₃)=C(CH₃)—CH₃ | |
| A-478 | CH₂—CH(CH₂—CH₃)—C(=CH₂)—CH₃ | |
| A-479 | C(=CH—CH₃)—CH₂—CH(CH₃)—CH₃ | |
| A-480 | CH(CH=CH₂)—CH₂—CH(CH₃)—CH₃ | |
| A-481 | C(CH₂—CH₃)=CH—CH(CH₃)—CH₃ | |
| A-482 | CH(CH₂—CH₃)CH=C(CH₃)—CH₃ | |
| A-483 | CH(CH₂—CH₃)CH₂—C(=CH₂)—CH₃ | |
| A-484 | C(=CH—CH₃)CH(CH₃)—CH₂—CH₃ | |
| A-485 | CH(CH=CH₂)CH(CH₃)—CH₂—CH₃ | |
| A-486 | C(CH₂—CH₃)=C(CH₃)—CH₂—CH₃ | |
| A-487 | CH(CH₂—CH₃)—C(=CH₂)—CH₂—CH₃ | |
| A-488 | CH(CH₂—CH₃)—C(CH₃)=CH—CH₃ | |
| A-489 | CH(CH₂—CH₃)—CH(CH₃)—CH=CH₂ | |
| A-490 | C(CH₃)(CH=CH₂)—CH₂—CH₂—CH₃ | |
| A-491 | C(CH₃)(CH₂—CH₃)—CH=CH—CH₃ | |
| A-492 | C(CH₃)(CH₂—CH₃)—CH₂—CH=CH₂ | |
| A-493 | C[=C(CH₃)—CH₃]—CH₂—CH₂—CH₃ | |
| A-494 | CH[C(=CH₂)—CH₃]—CH₂—CH₂—CH₃ | |
| A-495 | C(i-C₃H₇)=CH—CH₂—CH₃ | |
| A-496 | CH(i-C₃H₇)—CH=CH—CH₃ | |
| A-497 | CH(i-C₃H₇)—CH₂—CH=CH₂ | |
| A-498 | C(=CH—CH₃)—C(CH₃)₃ | |
| A-499 | CH(CH=CH₂)—C(CH₃)₃ | |
| A-500 | C(CH₃)(CH=CH₂)CH(CH₃)—CH₃ | |
| A-501 | C(CH₃)(CH₂—CH₃)C(=CH₂)—CH₃ | |
| A-502 | 2-CH₃-cyclohex-1-enyl | |
| A-503 | [2-(=CH₂)]-c-C₆H₉ | |
| A-504 | 2-CH₃-cyclohex-2-enyl | |
| A-505 | 2-CH₃-cyclohex-3-enyl | |
| A-506 | 2-CH₃-cyclohex-4-enyl | |
| A-507 | 2-CH₃-cyclohex-5-enyl | |
| A-508 | 2-CH₃-cyclohex-6-enyl | |
| A-509 | 3-CH₃-cyclohex-1-enyl | |
| A-510 | 3-CH₃-cyclohex-2-enyl | |
| A-511 | [3-(CH₂)]-c-C₆H₉ | |
| A-512 | 3-CH₃-cyclohex-3-enyl | |
| A-513 | 3-CH₃-cyclohex-4-enyl | |
| A-514 | 3-CH₃-cyclohex-5-enyl | |
| A-515 | 3-CH₃-cyclohex-6-enyl | |
| A-516 | 4-CH₃-cyclohex-1-enyl | |
| A-517 | 4-CH₃-cyclohex-2-enyl | |
| A-518 | 4-CH₃-cyclohex-3-enyl | |
| A-519 | [4-(=CH₂)]-c-C₆H₉ | |

The compounds of the formula I according to the invention are suitable for controlling harmful fungi and animal pests from the class of the insects, arachnids and nematodes. They can be used as fungicides and pesticides in crop protection and in the sectors of hygiene and of the protection of stored products and in the veterinary sector.

The Harmful Insects Include:

from the order of the lepidopterons (Lepidoptera), for example *Adoxophyes orana, Agrotis ypsilon, Agrotis segetum, Alabama argillacea, Anticarsia gemmatalis, Argyresthia conjugella, Autographa gamma, Cacoecia murinana, Capua reticulana, Choristoneura fumiferana, Chilo partellus, Choristoneura occidentalis, Cirphis unipuncta, Cnaphalocrocis medinalis, Crocidolomia binotalis, Cydia pomonella, Dendrolimus pini, Diaphania nitidalis, Diatraea grandiosella, Earias insulana, Elasmopalpus lignosellus, Eupoecilia ambiguella, Feltia subterranea, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera scitella, Lithocolletis blancardella, Lobesia botrana, Loxostege sticticalis, Lymantria dispar, Lymantria monacha, Lyonetia clerkella, Manduca sexta, Malacosoma neustria, Mamestra brassicae, Mocis repanda, Operophthera brumata, Orgyia pseudotsugata, Ostrinia nubilalis, Pandemis heparana, Panolis flammea, Pectinophora gossypiella, Phthorimaea operculella, Phyllocnistis citrella, Pieris brassicae, Plathypena scabra, Platynota stultana, Plutella xylostella, Prays citri, Prays oleae, Prodenia sunia, Prodenia ornithogalli, Pseudoplusia includens, Rhyacionia frustrana, Scrobipalpula absoluta, Sesamia inferens, Sparganothis pilleriana, Spodoptera frugiperda, Spodoptera littoralis, Spodoptera litura, Syllepta derogata, Synanthedon myopaeformis, Thaumatopoea pityocampa, Tortrix*

*viridana, Trichoplusia ni, Tryporyza incertulas, Zeiraphera canadensis*, furthermore *Galleria mellonella* and *Sitotroga cerealella, Ephestia cautella, Tineola bisselliella;* from the order of the beetles (Coleoptera), for example *Agriotes lineatus, Agriotes obscurus, Anthonomus grandis, Anthonomus pomorum, Apion vorax, Atomaria linearis, Blastophagus piniperda, Cassida nebulosa, Cerotoma trifurcata, Ceuthorhynchus assimilis, Ceuthorhynchus napi, Chaetocnema tibialis, Conoderus vespertinus, Crioceris asparagi, Dendroctonus refipennis, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otioffhynchus ovatus, Phaedon cochleariae, Phyllopertha horticola, Phyllophaga sp., Phyllotreta chrysocephala, Phyllotreta nemorum, Phyllotreta striolata, Popillia japonica, Psylliodes napi, Scolytus intricatus, Sitona lineatus,* furthermore *Bruchus rufimanus, Bruchus pisorum, Bruchus lentis, Sitophilus granaria, Lasioderma serricorne, Oryzaephilus surinamensis, Rhyzopertha dominica, Sitophilus oryzae, Tribolium castaneum, Trogoderma granarium, Zabrotes subfasciatus;* from the order of the dipterons (Diptera), for example *Anastrepha ludens, Ceratitis capitata, Contarinia sorghicola, Dacus cucurbitae, Dacus oleae, Dasineura brassicae, Delia coarctata, Delia radicum, Hydrellia griseola, Hylemyia platura, Liriomyza sativae, Liriomyza trifolii, Mayetiola destructor, Orseolia oryzae, Oscinella frit, Pegomya hyoscyami, Phorbia antiqua, Phorbia brassicae, Phorbia coarctata, Rhagoletis cerasi, Rhagoletis pomonella, Tipula oleracea, Tipula paludosa*, furthermore *Aedes aegypti, Aedes vexans, Anopheles maculipennis, Chrysomya bezziana, Chrysomya hominivorax, Chrysomya macellaria, Cordylobia anthropophaga, Culex pipiens, Fannia canicularis, Gasterophilus intestinalis, Glossina morsitans, Haematobia irritans, Haplodiplosis equestris, Hypoderma lineata, Lucilia caprina, Lucilia cuprina, Lucilia sericata, Musca domestica, Muscina stabulans, Oestrus ovis, Tabanus bovinus, Simulium damnosum;* from the order of the thrips (Thysanoptera), for example *Frankliniella fusca, Frankliniella occidentalis, Frankliniella tritici, Haplothrips tritici, Scirtothrips citri, Thrips oryzae, Thrips palmi, Thrips tabaci;* from the order of the hymenopterans (Hymenoptera), for example *Athalia rosae, Atta cephalotes, Atta sexdens, Atta texana, Hoplocampa minuta, Hoplocampa testudinea, Iridomyrmes humilis, Iridomyrmex purpureus, Monomorium pharaonis, Solenopsis geminata, Solenopsis invicta, Solenopsis richteri;* from the order of the heteropterans (Heteroptera), for example *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus hesperus, Lygus lineolaris, Lygus pratensis, Nezara viridula, Piesma quadrata, Solubea insularis, Thyanta perditor;* from the order of the homopterans (Homoptera), for example *Acyrthosiphon onobrychis, Acyrthosiphon pisum, Adelges laricis, Aonidiella aurantii, Aphidula nasturtii, Aphis fabae, Aphis gossypii, Aphis pomi, Aulacorthum solani, Bemisia tabaci, Brachycaudus cardui, Brevicoryne brassicae, Dalbulus maidis, Dreyfusia nordmannianae, Dreyfusia piceae, Dysaphis radicola, Empoasca fabae, Eriosoma lanigerum, Laodelphax striatella, Macrosiphum avenae, Macrosiphum euphorbiae, Macrosiphon rosae, Megoura viciae, Metopolophium dirhodum, Myzus persicae, Myzus cerasi, Nephotettix cincticeps, Nilaparvata lugens, Perkinsiella saccharicida, Phorodon humuli, Planococcus citri, Psylla mali, Psylla piri, Psylla pyricol, Quadraspidiotus perniciosus, Rhopalosiphum maidis, Saissetia oleae, Schizaphis graminum, Selenaspidus articulatus, Sitobion avenae, Sogatella furcifera, Toxoptera citricida, Trialeurodes abutilonea, Trialeurodes vaporariorum, Viteus vitifolii,* from the order of the termites (Isoptera), for example *Calotermes flavicollis, Leucotermes flavipes, Macrotermes subhyalinus, Odontotermes formosanus, Reticulitermes lucifugus, Termes natalensis;* from the order of the orthopterans (Orthoptera), for example *Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Schistocerca americana, Schistocerca peregrina, Stauronotus maroccanus, Schistocerca gregaria,* furthermore *Acheta domestica, Blatta orientalis, Blattella germanica, Periplaneta americana;* from the order of the Arachnoidea, for example phytophagous mites, such as *Aculops lycopersicae, Aculops pelekassi, Aculus schlechtendali, Brevipalpus phoenicis, Bryobia praetiosa, Eotetranychus carpini, Eutetranychus banksii, Eriophyes sheldoni, Oligonychus pratensis, Panonychus ulmi, Panonychus citri, Phyllocoptruta oleivora, Polyphagotarsonemus latus, Tarsonemus pallidus, Tetranychus cinnabarinus, Tetranychus kanzawai, Tetranchus pacificus, Tetranychus urticae,* ticks, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Rhipicephalus appendiculatus* and *Rhipicephalus evertsi*, and also mites which are parasites to animals, such as *Dermanyssus gallinae, Psoroptes ovis* and *Sarcoptes scabiei,* from the class of the nematodes, for example root gall nematodes, for example *Meloidogyne hapla, Meloidogyne incognita, Meloidogyne javanica*, cyst-forming nematodes, for example *Globodera pallida, Globodera rostochiensis, Heterodera avenae, Heterodera glycines, Heterodera schachtii*, migratory endoparasites and semi-endoparasitic nematodes, for example *Heliocotylenchus multicinctus, Hirschmanniella oryzae, Hoplolaimus* spp, *Pratylenchus brachyurus, Pratylenchus fallax, Pratylenchus penetrans, Pratylenchus vulnus, Radopholus similis, Rotylenchus reniformis, Scutellonema bradys, Tylenchulus semipenetrans*, stem and leaf nematodes, for example *Anguina tritici, Aphelenchoides besseyi, Ditylenchus angustus, Ditylenchus dipsaci*, virus vectors, for example *Longidorus* spp, *Trichodorus christei, Trichodorus viruliferus, Xiphinema index, Xiphinema mediterraneum.*

The compounds I can be applied as such, in the form of their formulations or in the use forms prepared therefrom, for example in the form of directly sprayable solutions, powders, suspensions or dispersions, emulsions, oil dispersions, pastes, dustable products, compositions for broadcasting, granules, by spraying, atomizing, dusting, broadcasting or watering. The application forms depend entirely on the intended uses; in each case, they should ensure a very fine distribution of the active compounds according to the invention.

The compounds I are particularly suitable as fungicides. They are distinguished through an outstanding effectiveness against a broad spectrum of phytopathogenic fungi, especially from the classes of the Ascomycetes, Deuteromycetes, Oomycetes and Basidiomycetes. Some are systemically effective and they can be used in plant protection as foliar fungicides, fungicides for seed dressing and soil fungicides.

They are particularly important in the control of a multitude of fungi on various cultivated plants, such as wheat, rye, barley, oats, rice, maize, grass, bananas, cotton, soya, coffee, sugar cane, vines, fruits and ornamental plants, and vegetables, such as cucumbers, beans, tomatoes, potatoes and cucurbits, and on the seeds of these plants.

They are especially suitable for controlling the following plant diseases:

*Alternaria* species on fruit and vegetables,
*Bipolaris* and *Drechslera* species on cereals, rice and lawns,
*Blumeria graminis* (powdery mildew) on cereals,
*Botrytis cinerea* (gray mold) on strawberries, vegetables, ornamental plants and grapevines,
*Bremia lactucae* on lettuce,
*Erysiphe cichoracearum* and *Sphaerotheca fuliginea* on cucurbits,
*Fusarium* and *Verticillium* species on various plants,
*Mycosphaerella* species on cereals, bananas and peanuts,
*Peronospora* species on cabbage and onion plants,
*Phakospora pachyrhizi* and *P. meibomiae* on soya,
*Phytophthora infestans* on potatoes and tomatoes,
*Phytophthora capsici* on peppers,
*Plasmopara viticola* on grapevines,
*Podosphaera leucotricha* on apples,
*Pseudocercosporella herpotrichoides* on wheat and barley,
*Pseudoperonospora* species on hops and cucumbers,
*Puccinia* species on cereals,
*Pyricularia oryzae* on rice,
*Pythium aphanidermatum* on lawns,
*Rhizoctonia* species on cotton, rice and lawns,
*Septoria tritici* and *Stagonospora nodorum* on wheat,
*Uncinula necator* on grapevines,
*Ustilago* species on cereals and sugar cane, and
*Venturia* species (scab) on apples and pears.

The compounds I are also suitable for controlling harmful fungi, such as *Paecilomyces variotii*, in the protection of materials (for example wood, paper, paint dispersions, fibers or fabrics) and in the protection of stored products.

In addition, the compounds of the formula I can also be used in crops which are tolerant to attack by insects or fungi by virtue of breeding, including genetic engineering methods.

The compounds I are employed by treating the fungi or the plants, seeds, materials or soil to be protected from fungal attack with a fungicidally effective amount of the active compounds. The application can be carried out both before and after the infection of the materials, plants or seeds by the fungi.

The fungicidal compositions generally comprise between 0.1 and 95%, preferably between 0.5 and 90%, by weight of active compound.

When employed in plant protection, the amounts applied are, depending on the kind of effect desired, between 0.01 and 2.0 kg of active compound per ha.

In seed treatment, amounts of active compound of 0.001 to 0.1 g, preferably 0.01 to 0.05 g, per kilogram of seed are generally necessary.

When used in the protection of materials or stored products, the amount of active compound applied depends on the kind of application area and on the desired effect. Amounts customarily applied in the protection of materials are, for example, 0.001 g to 2 kg, preferably 0.005 g to 1 kg, of active compound per cubic meter of treated material.

The compounds I can be converted to the customary formulations, for example solutions, emulsions, suspensions, dusts, powders, pastes and granules. The application form depends on the particular intended use; it should in any case ensure a fine and uniform distribution of the compound according to the invention.

The formulations are prepared in a known manner, for example by extending the active compound with solvents and/or carriers, if desired using emulsifiers and dispersants. Solvents/auxiliaries which are suitable are essentially:

Water, aromatic solvents (for example Solvesso products, xylene), paraffins (for example mineral fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

carriers such as ground natural minerals (for example kaolins, clays, talc, chalk) and ground synthetic minerals (for example highly disperse silica, silicates); emulsifiers such as nonionic and anionic emulsifiers (for example polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound. The active compounds are employed in a purity of from 90% to 100%, preferably 95% to 100% (according to NMR spectrum).

The following are examples of formulations: 1. Products for dilution with water

A) Water-soluble Concentrates (SL)

10 parts by weight of a compound according to the invention are dissolved in water or in a water-soluble solvent. As an alternative, wetters or other auxiliaries are added. The active compound dissolves upon dilution with water.

B) Dispersible Concentrates (DC)

20 parts by weight of a compound according to the invention are dissolved in cyclohexanone with addition of a dispersant, for example polyvinylpyrrolidone. Dilution with water gives a dispersion.

C) Emulsifiable Concentrates (EC)

15 parts by weight of a compound according to the invention are dissolved in xylene with addition of calcium dodecylbenzenesulfonate and castor oil ethoxylate (in each case 5% strength). Dilution with water gives an emulsion.

D) Emulsions (EW, EO)

40 parts by weight of a compound according to the invention are dissolved in xylene with addition of calcium dodecylbenzenesulfonate and castor oil ethoxylate (in each case 5% strength). This mixture is introduced into water by means of an emulsifier (Ultraturrax) and made into a homogeneous emulsion. Dilution with water gives an emulsion.

E) Suspensions (SC, OD)

In an agitated ball mill, 20 parts by weight of a compound according to the invention are comminuted with addition of dispersants, wetters and water or an organic solvent to give a fine active compound suspension. Dilution with water gives a stable suspension of the active compound.

F) Water-dispersible Granules and Water-soluble Granules (WG, SG)

50 parts by weight of a compound according to the invention are ground finely with addition of dispersants and wetters and made into water-dispersible or water-soluble granules by means of technical appliances (for example extrusion, spray tower, fluidized bed). Dilution with water gives a stable dispersion or solution of the active compound.

G) Water-dispersible Powders and Water-soluble Powders (WP, SP)

75 parts by weight of a compound according to the invention are ground in a rotor-stator mill with addition of dispersants, wetters and silica gel. Dilution with water gives a stable dispersion or solution of the active compound.

2. Products to be Applied Undiluted

H) Dustable Powders (DP)

5 parts by weight of a compound according to the invention are ground finely and mixed intimately with 95% of finely divided kaolin. This gives a dustable product.

I) Granules (GR, FG, GG, MG)

0.5 part by weight of a compound according to the invention is ground finely and associated with 95.5% carriers. Current methods are extrusion, spray-drying or the fluidized bed. This gives granules to be applied undiluted.

J) ULV Solutions (UL)

10 parts by weight of a compound according to the invention are dissolved in an organic solvent, for example xylene. This gives a product to be applied undiluted.

The active compounds can be used as such, in the form of their formulations or of the application forms prepared therefrom, e.g. in the form of directly sprayable solutions, powders, suspensions or dispersions, emulsions, oil dispersions, pastes, dusts, preparations for broadcasting or granules, by spraying, atomizing, dusting, broadcasting or watering. The application forms depend entirely on the intended uses; they should always ensure the finest possible dispersion of the active compounds according to the invention.

Aqueous application forms can be prepared from emulsifiable concentrates, pastes or wettable powders (spray powders, oil dispersions) by addition of water. To prepare emulsions, pastes or oil dispersions, the substances can be homogenized in water, as such or dissolved in an oil or solvent, by means of wetting agents, tackifiers, dispersants or emulsifiers. However, it is also possible to prepare concentrates comprising active substance, wetting agent, tackifier, dispersant or emulsifier and possibly solvent or oil which are suitable for dilution with water.

The concentrations of active compound in the ready-for-use preparations can be varied within relatively wide ranges. In general, they are between 0.0001 and 10%, preferably between 0.01 and 1%.

The active compounds can also be used with great success in the ultra-low volume (ULV) process, it being possible to apply formulations with more than 95% by weight of active compound or even the active compound without additives.

Oils of various types, wetting agents, adjuvants, herbicides, fungicides, other pesticides and bactericides can be added to the active compounds, if need be also not until immediately before use (tank mix). These agents can be added to the preparations according to the invention in a weight ratio of 1:10 to 10:1.

The preparations according to the invention can, in the application form as fungicides, also be present together with other active compounds, e.g. with herbicides, insecticides, growth regulators, fungicides or also with fertilizers. On mixing the compounds I or the preparations comprising them in the application form as fungicides with other fungicides, in many cases an expansion of the fungicidal spectrum of activity is obtained.

The following list of fungicides, with which the compounds according to the invention can be used in conjunction, is intended to illustrate the possible combinations but does not limit them:

acylalanines, such as benalaxyl, metalaxyl, ofurace or oxadixyl, amine derivatives, such as aldimorph, dodine, dodemorph, fenpropimorph, fenpropidin, guazatine, iminoctadine, spiroxamine or tridemorph, anilinopyrimidines, such as pyrimethanil, mepanipyrim or cyprodinyl, antibiotics, such as cycloheximide, griseofulvin, kasugamycin, natamycin, polyoxin or streptomycin, azoles, such as bitertanol, bromoconazole, cyproconazole, difenoconazole, dinitroconazole, enilconazole, epoxiconazole, fenbuconazole, fluquinconazole, flusilazole, flutriafol, hexaconazole, imazalil, ipconazole, metconazole, myclobutanil, penconazole, propiconazole, prochloraz, prothioconazole, simeconazole, tebuconazole, tetraconazole, triadimefon, triadimenol, triflumizole or triticonazole, dicarboximides, such as iprodione, myclozolin, procymidone or vinclozolin, dithiocarbamates, such as ferbam, nabam, maneb, mancozeb, metam, metiram, propineb, polycarbamate, thiram, ziram or zineb, heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, penthiopyrad, probenazole, proquinazid, pyrifenox, pyroquilon, quinoxyfen, silthiofam, thiabendazole, thifluzamide, thiophanate-methyl, tiadinil, tricyclazole, triforine or 5-chloro-7-(4-methylpiperidin-1-yl)-6-(2,4,6-trifluorophenyl)-[1,2,4]-triazolo[1,5-a]pyrimidine, copper fungicides, such as Bordeaux mixture, copper acetate, copper oxychloride or basic copper sulfate, nitrophenyl derivatives, such as binapacryl, dinocap, dinobuton or nitrophthal-isopropyl, phenylpyrroles, such as fenpiclonil or fludioxonil, sulfur, other fungicides, such as acibenzolar-S-methyl, benthiavalicarb, carpropamid, chlorothalonil, cyflufenamid, cymoxanil, diclomezine, diclocymet, diethofencarb, edifenphos, ethaboxam, fenhexamid, fentin acetate, fenoxanil, ferimzone, fluazinam, fosetyl, fosetyl-aluminum, iprovalicarb, hexachlorobenzene, metrafenone, pencycuron, phosphorous acid, propamocarb, phthalide, tolclofos-methyl, quintozene or zoxamide, strobilurins, such as azoxystrobin, dimoxystrobin, enestroburin, fluoxastrobin, kresoxim-methyl, metominostrobin, orysastrobin, picoxystrobin, pyraclostrobin or trifloxystrobin, sulfenic acid derivatives, such as captafol, captan, dichlofluanid, folpet or tolylfluanid, cinnamides and analogous compounds, such as dimethomorph, flumetover or flumorph.

SYNTHESIS EXAMPLES

Preparation of the Starting Materials

Example A 3-(2-Chloro-6-fluorophenyl)-2,4-dichloro-6-([1,2,4]triazol-1-yl)pyridine (Table B, No. V-2)

Aa) 2-Chloro-3-(2-chloro-6-fluorophenyl)-4,6-dihydroxypyridine 94.0 g (0.55 mol) of 2-chloro-6-fluorophenylacetonitrile and 160 ml malonyl chloride were stirred at room temperature for 8 days, during which time the mixture slowly solidified. For work-up, the mixture was stirred with cyclohexane and filtered off, and the residue washed twice with in each case 25 ml methylene chloride. With ice-cooling, the residue was then dissolved in 20% strength aqueous sodium hydroxide solution and washed twice with methylene chloride. With ice-cooling, the aqueous phase was then acidified with concentrated hydrochloric acid. The residue was filtered off, washed with a little water and dried under reduced pressure. Yield 150 g.

Ab) 3-(2-Chloro-6-fluorophenyl)-2,4,6-trichloropyridine 40.0 g (0.146 mol) of 2-chloro-3-(2-chloro-6-fluorophenyl)-4,6-dihydroxypyridine and 27.9 g (0.292 mol) of trimethylamine hydrochloride were added to 89.5 g (0.584 mol) phosphoryl chloride and the mixture was, in a tantalum autoclave, heated under intrinsic pressure at 120° C. for 12 h. The reaction mixture was flushed out of the autoclave with toluene and concentrated under reduced pressure. This gave a residue of 100 g. This crude product was purified by silica gel column chomatography using cyclohexane/ethyl acetate (5:1). Finally, the product was stirred with pentane. $^1$H-NMR (CDCl$_3$): 7.15 (t); 7.37 (d); 7.44 (m); 7.50 (s).

Ac) 3-(2-Chloro-6-fluorophenyl)-2,4-dichloro-6-([1,2,4]triazol-1-yl)pyridine 0.42 g (11.0 mmol) of 60% sodium hydride in paraffin was added a little at a time to 3.00 g (9.6 mmol) of 3-(2-chloro-6-fluorophenyl)-2,4,6-trichloropyridine and 0.70 g (9.6 mmol) of [1,2,4]triazole dissolved in 30 ml of dimethylformamide. The mixture was stirred at room temperature for 3 d, added to 50 ml of sodium dihydrogenphosphate solution, extracted three times with in each case 50 ml of methyl tert-butyl ether, dried over sodium sulfate and concentrated under reduced pressure. The crude product was chromatographed on silica gel using cyclohexane/ethyl acetate. Yield 1.5 g of a colorless solid of m.p. 210° C.

Example B 3-(2-Chloro-6-fluorophenyl)-2,4-dichloro-6-(pyridin-2-yl)pyridine (Table B, No. V-3)

64.8 g (0.26 mol) of 3-(2-chloro-6-fluorophenyl)-2,4,6-trichloropyridine (see Example Ab), 83.6 g (0.29 mol) 2-tri-n-butylstannylpyridine and 4.8 g (5.2 mmol) tetrakistriphenylphosphinepalladium(0), dissolved in 600 ml of dimethylformamide and 400 ml 1,4-dioxane, were boiled under reflux for 8 h and then stirred at room temperature overnight. The volatile components were removed under reduced pressure, and 400 ml of water were then added, the mixture was extracted five times with in each case 150 ml of methyl tert-butyl ether and the combined extracts were washed once with 100 ml of saturated sodium chloride solution, dried over sodium sulfate and concentrated under reduced pressure. The crude product was chromatographed on silica gel using cyclohexane/ethyl acetate and triturated with n-pentane. Yield 36.0 g of a colorless solid of m.p. 45° C.

Example C 3-(2-Chloro-6-fluorophenyl)-2,4-dichloro-6-(pyrimidin-2-yl)pyridine (Table B, No. V-6)

14.6 g (0.047 mol) of 3-(2-chloro-6-fluorophenyl)-2,4,6-trichloropyridine (see Example Ab), 20.0 g (0.051 mol) of 2-tri-n-butylstannylpyrimidine and 1.1 g (0.94 mmol) of tetrakistriphenylphosphinepalladium(0), dissolved in 70 ml of dimethylformamide and 50 ml of 1,4-dioxane, were kept at 110° C. for 10 h. After removal of the volatile components under reduced pressure, the product was purified on silica gel using cyclohexane/ethyl acetate. Yield 2.0 g of yellow crystals (m.p. 147° C.).

Example D

5-Bromo-3-(2-chloro-6-fluorophenyl)-2,4,6-trichloropyridine (Table B, No. V-8)

At room temperature, 2.0 g (22.4 mmol) of N,N-dimethylaminoethanol were added to 2.0 g (6.4 mmol) of 3-(2-chloro-6-fluorophenyl)-2,4,6-trichloropyridine (see Example Ab) dissolved in 25 ml of tetrahydrofuran, and the mixture was cooled to −78° C. 26 ml (41.9 mmol) of n-butyllithium (1.6 M in hexane) were then added dropwise, and the mixture was stirred at −75° C. to −50° C. for 1.5 h. 4.0 g (15.4 mmol) of 1,2-dibromotetra-fluoroethane were then added dropwise, and the mixture was stirred at −50° C. to −70° C. for 1 h, thawed to room temperature, added to 70 ml of 10% strength hydrochloric acid, extracted three times with in each case 80 ml of methyl tert-butyl ether, dried over sodium sulfate, concentrated under reduced pressure and triturated with hexane. Yield 1.6 g. $^1$H-NMR (CDCl$_3$) δ=7.15 (m); 7.40 (m).

Example E

5-Bromo-3-(2-chloro-6-fluorophenyl)-2,4-dichloro-6-methylthiopyridine 1.6 g (4.1 mmol) of 5-bromo-3-(2-chloro-6-fluorophenyl)-2,4,6-trichloropyridine (Example D) and 300 mg (4.1 mmol) of sodium methylthiolate, dissolved in 30 ml of tetrahydrofuran, were boiled under reflux for 5 h. The mixture was added to 50 ml of water, extracted three times with in each case 50 ml of diethyl ether, dried over sodium sulfate, concentrated under reduced pressure and chromatographed on silica gel using cyclohexane/ethyl acetate. Yield 1.13 g of an oil. $^1$H-NMR (CDCl$_3$) δ=2.60 (s); 7.15 (m); 7.40 (m).

Example F

5-Bromo-3-(2-chloro-6-fluorophenyl)-2,4-dichloro-6-methylsulfonylpyridine

At room temperature, 50 mg (0.1 mmol) of sodium tungstate were added to 1.1 g (2.7 mmol) of 5-bromo-3-(2-chloro-6-fluorophenyl)-2,4-dichloro-6-methylthiopyridine (Example E) dissolved in 10 ml of glacial acetic acid, and 0.78 g (6.9 mmol) of 30% strength hydrogen peroxide were then added dropwise. The mixture was stirred at room temperature overnight, added to 50 ml of ice-water, extracted three times with in each case 50 ml methyl tert-butyl ether, washed once with 20 ml of sodium carbonate solution, dried over sodium sulfate and concentrated under reduced pressure. Yield 1.07 g. $^1$H-NMR (CDCl$_3$) δ=3.50 (s); 7.17 (m); 7.40 (m).

Example G

5-Bromo-3-(2-chloro-6-fluorophenyl)-6-cyano-2,4-dichloropyridine

At room temperature, a spatula tip (about 10 mg) of crown ether (18-crown-6) and 1 ml of dimethyl sulfoxide were added to 1.65 g (3.8 mmol) of 5-bromo-3-(2-chloro-6-fluorophenyl)-2,4-dichloro-6-methylsulfonylpyridine (Example F) dissolved in 50 ml of acetonitrile, and the mixture was heated to 60° C. Over a period of 6 h, 500 mg (7.6 mmol) of potassium cyamide were then added a little at a time at this temperature. The mixture was stirred at room temperature overnight and chromatographed directly on silica gel using cyclohexane/ethyl acetate. Yield 0.57 g of a solid, m.p. 90° C. $^1$H-NMR (CDCl$_3$) δ=7.18 (m); 7.40 (m).

Example H

3-Bromo-5-(2-chloro-6-fluorophenyl)-4,6-dichloro-2-pyridine-carboxamidoxime (Table B, V-14)

300 mg (0.79 mmol) of 5-bromo-3-(2-chloro-6-fluorophenyl)-6-cyano-2,4-dichloropyridine (Example G), 70 mg (1.0 mmol) of hydroxylamine hydrochloride and 50 mg (0.63 mmol) of sodium bicarbonate, dissolved in 10 ml of ethanol and 2 ml of water, were stirred at room temperature overnight at room temperature, and another 70 mg (1.0 mmol) of hydroxylamine hydrochloride and 50 mg (0.63 mmol) of sodium bicarbonate were then added and the mixture was again stirred at room temperature overnight. The mixture was concentrated under reduced pressure, 30 ml of water were added, and the mixture was extracted three times with in each case 50 ml of methyl tert-butyl ether, dried over sodium sulfate and concentrated under reduced pressure. Yield 340 mg, m.p. 132° C. $^1$H-NMR (CDCl$_3$) δ=5.40 (broad); 7.18 (m); 7.40 (m); 7.60 (broad).

The intermediates V of Table B were prepared analogously to Examples A to H. To this end, 3-(2-chloro-6-fluorophenyl)-2,4,6-trichloropyridine (see Example Ab) was reacted with the appropriate nucleophiles.

TABLE B

| | intermediates V | |
|---|---|---|
| No. | Formula | Phys. data |
| V-1 | 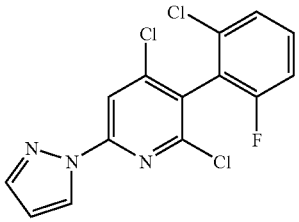 | m.p. 55° C. |

TABLE B-continued intermediates V

| No. | Formula | Phys. data |
| --- | --- | --- |
| V-2 | | m.p. 210° C. |
| V-3 | | m.p. 45° C. |
| V-4 | | $^1$H-NMR (CDCl$_3$) δ = 7.15-7.50 (m); 7.55 (6); 7.97 (d); 8.30 (s). |
| V-5 | | m.p. 152° C. |
| V-6 | | m.p. 147° C. |
| V-7 | | m.p. 153° C. |

TABLE B-continued
intermediates V
| No. | Formula | Phys. data |
|---|---|---|
| V-8 | 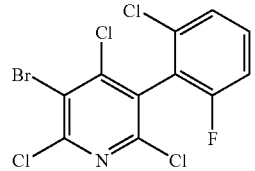 | m.p. 118-120° C. |
| V-9 | 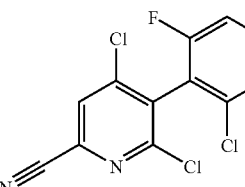 | m.p. 56° C. |
| V-10 | 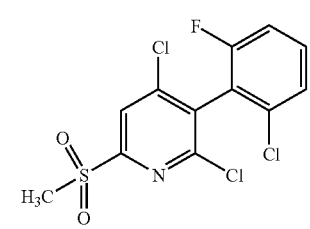 | m.p. 94° C. |
| V-11 | 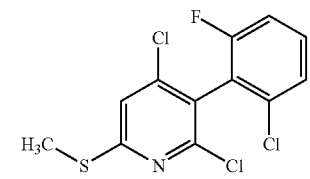 | m.p. 105° C. |
| V-12 | 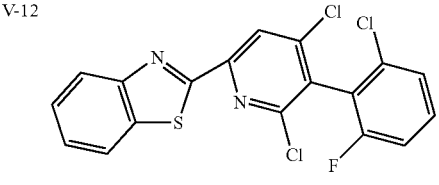 | m.p. 199° C. |
| V-13 | 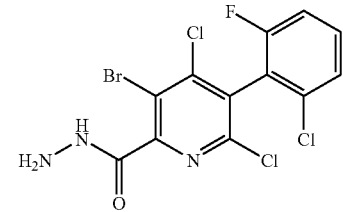 | m.p. 153-156° C. |
| V-14 | 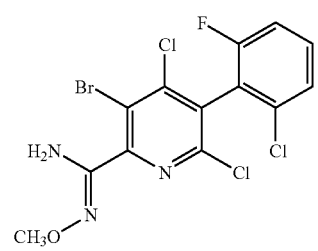 | m.p. 132° C. |

Syntheses of Active Compounds

Example 1

2-Chloro-3-(2-chloro-6-fluorophenyl)-4-(2-propylamino)-6-([1,2,4]triazol-1-yl)pyridine and 4-chloro-3-(2-chloro-6-fluorophenyl)-2-(2-propylamino)-6-([1,2,4]triazol-1-yl)pyridine (Table C, No. I-13, I-14)

In a stainless steel autoclave, 700 mg (2.0 mmol) of 3-(2-chloro-6-fluorophenyl)-2,4-dichloro-6-([1,2,4]triazolyl)pyridine (Example A) and 15 g of diisopropylamine were heated at 160° C. for 12 h. The volatile components were removed under reduced pressure and the residue was chromatographed on silica gel using cyclohexane/ethyl acetate. It was possible to isolate 240 mg of 2-chloro-3-(2-chloro-6-fluorophenyl)-4-(2-propylamino)-6-([1,2,4]triazolyl)pyridine (m.p. 152° C.) and 310 mg of 4-chloro-3-(2-chloro-6-fluorophenyl)-2-(2-propylamino)-6-([1,2,4]triazolyl)pyridine (m.p. 152° C.).

Example 2

2-Chloro-3-(2-chloro-6-fluorophenyl)-4-(2-butylamino)-6-(pyridin-2-yl)pyridine and 4-chloro-3-(2-chloro-6-fluorophenyl)-2-(2-butylamino)-6-(pyridin-2-yl)pyridine (Table B, No. I-43, I-44)

In a stainless steel autoclave, 2.0 g (5.7 mmol) of 3-(2-chloro-6-fluorophenyl)-2,4-dichloro-6-(pyridin-2-yl)pyridine (Example B) and 15 g of racemic 2-butylamine were heated at 180° C. for 12 h. The volatile components were removed under reduced pressure and the residue was chromatographed on silica gel using cyclohexane/ethyl acetate. It was possible to isolate 450 mg of 4-chloro-3-(2-chloro-6-fluorophenyl)-2-(2-butylamino)-6-(pyridin-2-yl)pyridine ($^1$H-NMR (CDCl$_3$) δ=0.90 (m); 1.20 (m); 1.55 (m); 3.80 (broad); 4.27 (m); 7.15-7.45 (m); 7.80 (t); 7.90 (s); 8.42 (d); 8.67 (m)) and 370 mg of 2-chloro-3-(2-chloro-6-fluorophenyl)-4-(2-butylamino)-6-(pyridin-2-yl)pyridine ($^1$H-NMR (CDCl$_3$) δ=0.90 (m); 1.20 (m); 1.50 (m); 3.67 (broad); 3.77 (m); 7.15-7.45 (m); 7.75 (s); 7.82 (t); 8.42 (d); 8.67 (m)). The compounds are present as rotamer mixtures.

Example 3

2-Chloro-3-(2-chloro-6-fluorophenyl)-4-(4-methylpiperidinyl)-6-(pyrimidin-2-yl)pyridine and 4-chloro-3-(2-chloro-6-fluorophenyl)-2-(4-methylpiperidinyl)-6-(pyrimidin-2-yl)pyridine (Table B, No. I-53, I-54)

In a stainless steel autoclave, 500 mg (1.4 mmol) of 3-(2-chloro-6-fluorophenyl)-2,4-dichloro-6-(pyrimidin-2-yl)pyridine (Example C) and 15 g of 4-methylpiperidin were heated at 140° C. for 12 h. The volatile components were removed under reduced pressure and the residue was chromatographed on silica gel using cyclohexane/ethyl acetate. It was possible to isolate 220 mg of 4-chloro-3-(2-chloro-6-fluorophenyl)-2-(4-methylpiperidinyl)-6-(pyrimidin-2-yl)pyridine (m.p. 129° C.) and 60 mg of 2-chloro-3-(2-chloro-6-fluorophenyl)-4-(4-methylpiperidinyl)-6-(pyrimidin-2-yl)pyridine (m.p. 129° C.).

TABLE C

| No. | Formula | Phys. data |
|---|---|---|
| I-1 | (structure) | $^1$H-NMR (CDCl$_3$) δ = 1.20 (t); 3.87 (d); 4.30 (m); 6.45 (m); 7.20 (t); 7.40 (m); 7.73 (m); 8.52 (m). |
| I-2 | (structure) | $^1$H-NMR (CDCl$_3$) δ = 1.22 (m); 3.75 (m); 3.88 (m); 6.45 (m); 7.15-7.40 (m); 7.75 (m); 8.55 (m). |

TABLE C-continued active compounds

| No. | Formula | Phys. data |
|---|---|---|
| I-3 | | |
| I-4 | | m.p. 170° C. |
| I-5 | | m.p. 78° C. |
| I-6 | | $^{1}$H-NMR (CDCl$_3$) δ = 0.85 (s); 1.05 (d); 3.50 (m); 3.88 (d); 6.42 (t); 7.20 (m); 7.40 (m); 7.75 (d); 8.55 (d) [mixture of rotamers]. |

TABLE C-continued active compounds

| No. | Formula | Phys. data |
|---|---|---|
| I-7 | | $^1$H-NMR (CDCl$_3$) δ = 0.85 and 0.87 (s); 1.05 and 1.06 (d); 3.90 (d); 4.20 (m); 6.47 (m); 7.20 (m); 7.40 (m); 7.73 (m); 8.50 (m) [mixture of rotamers]. |
| I-8 | | $^1$H-NMR (CDCl$_3$) δ = 0.75-2.25 (m); 3.22 (m); 3.78 (d); 6.45 (m); 7.18 (m); 7.40 (m); 7.74 (m); 8.55 (m) |
| I-9 | | m.p. 126° C. |
| I-10 | | $^1$H-NMR (CDCl$_3$) δ = 0.85 and 0.87 (d); 1.16 and 1.18 (d); 1.30 (m); 1.60 (m); 3.75 (m); 6.45 (m); 7.20 (m); 7.40 (m); 7.75 (m); 8.55 (m) [mixture of rotamers]. |

TABLE C-continued active compounds

| No. | Formula | Phys. data |
|---|---|---|
| I-11 | | $^1$H-NMR (CDCl$_3$) δ = 0.88 (m); 1.13 (m); 1.30 (m); 1.60 (m); 3.80 (m); 4.33 (m); 6.45 (m); 7.20 (m); 7.40 (m); 7.73 (m); 8.55 (m) [mixture of rotamers]. |
| I-12 | | $^1$H-NMR (CDCl$_3$) δ = 0.88 (m); 1.16 (m); 1.25 (m); 1.40 (m); 1.63 (m); 3.70 (m); 6.45 (m); 7.20 (m); 7.40 (m); 7.73 (m); 8.55 (m) [mixture of rotamers]. |
| I-13 | | m.p. 152° C. |
| I-14 | | m.p. 152° C. |
| I-15 | | m.p. 108° C. |

TABLE C-continued
active compounds
| No. | Formula | Phys. data |
|---|---|---|
| I-16 | 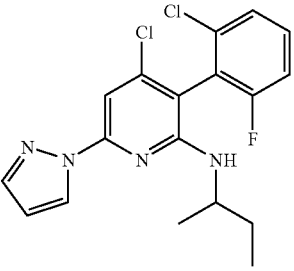 | m.p. 114° C. |
| I-17 | 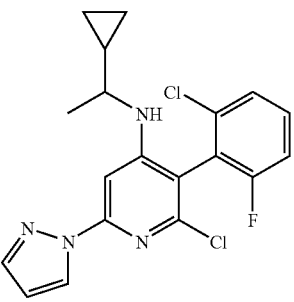 | $^1$H-NMR (CDCl$_3$) δ = 0.25 (m); 0.47 (m); 0.80 (m); 1.25 (m); 3.23 (m); 3.95 (m); 6.45 (m); 7.20 (m); 7.40 (m); 7.73 (m); 8.55 (m) [mixture of rotamers]. |
| I-18 | 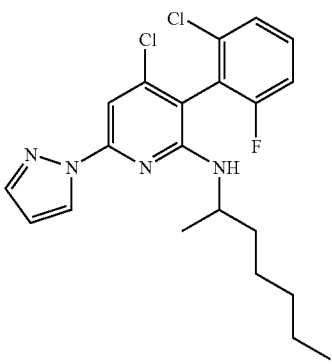 | $^1$H-NMR (CDCl$_3$) δ = 0.88 (m); 1.15 (m); 1.30 (m); 1.50 (m); 3.85 (m); 4.20 (m); 6.45 (m); 7.20 (m); 7.40 (m); 7.73 (m); 8.55 (m) [mixture of rotamers]. |
| I-19 | 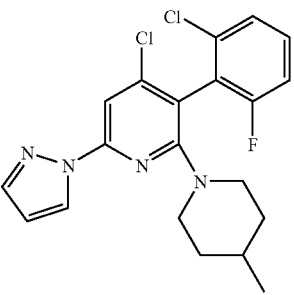 | m.p. 120° C. |
| I-20 | 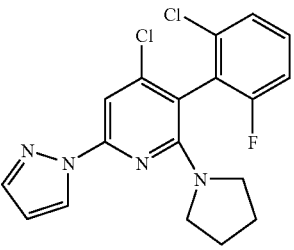 | m.p. 158° C. |

TABLE C-continued active compounds

| No. | Formula | Phys. data |
|---|---|---|
| I-21 | | m.p. 161° C. |
| I-22 | | m.p. 164° C. |
| I-23 | | m.p. 103° C. |
| I-24 | | m.p. 162° C. |
| I-25 | | m.p. 181° C. |

TABLE C-continued active compounds

| No. | Formula | Phys. data |
|---|---|---|
| I-26 | | $^1$H-NMR (CDCl$_3$) δ = 0.85 (s); 0.95-2.25 (m); 3.80 (d); 4.00 (m); 7.10 (t); 7.37 (m); 7.85 (t); 7.90 (s); 8.43 (d); 8.63 (m). |
| I-27 | | m.p. 163° C. |
| I-28 | | $^1$H-NMR (CDCl$_3$) δ = 1.20 (m); 3.72 (d); 3.96 (m); 7.13 (t); 7.33 (m); 7.40 (m); 7.75 (s); 7.80 (t); 8.45 (d); 8.70 (m). |
| I-29 | | $^1$H-NMR (CDCl$_3$) δ = 0.90 (s); 1.10 (m); 3.85 (d); 4.30 (m); 7.20 (m); 7.33 (m); 7.43 (m); 7.83 (m); 7.90 (s); 8.45 (d); 8.70 (m). |
| I-30 | | $^1$H-NMR (CDCl$_3$) δ = 0.88 (d); 0.95 (m); 1.50 (m); 2.80 (m); 7.10 (m); 7.33 (m); 7.80 (t); 8.10 (s); 8.45 (d); 8.70 (m). |

TABLE C-continued active compounds

| No. | Formula | Phys. data |
|---|---|---|
| I-31 | | m.p. 119° C. |
| I-32 | | |
| I-33 | | $^1$H-NMR (CDCl$_3$) δ = 0.25 (m); 0.45 (m); 0.80 (m); 1.22 (m); 3.30 (m); 3.90 (m); 7.13-7.45 (m); 7.70 (s); 7.80 (t); 8.45 (d); 8.70 (m) (mixture of rotamers). |
| I-34 | | $^1$H-NMR (CDCl$_3$) δ = 0.82 (m); 1.10-1.50 (m); 3.70 (m); 3.80 (m); 7.13-7.45 (m); 7.75 (s); 7.80 (t); 8.45 (d); 8.67 (m). |
| I-35 | | $^1$H-NMR (CDCl$_3$) δ = 1.00-1.75 (m); 2.10 (m); 3.90 (d); 4.15 (m); 7.13-7.45 (m); 7.80 (t); 7.87 (s); 8.40 (d); 8.70 (m). |

TABLE C-continued active compounds

| No. | Formula | Phys. data |
|---|---|---|
| I-36 | | m.p. 83° C. |
| I-37 | | $^1$H-NMR (CDCl$_3$) δ = 0.90 (m); 1.18(m); 1.25(m); 1.40 (m); 1.67 (m); 3.75 (m); 4.45 (m); 7.15-7.45 (m); 7.80 (t); 7.90 (s); 8.42 (d); 8.67 (m). |
| I-38 | | $^1$H-NMR (CDCl$_3$) δ = 0.90 (m); 1.18 (m); 1.25-1.40 (m); 1.62 (m); 3.63 (m); 3.85 (m); 7.15-7.45 (m); 7.76 (s); 7.80 (t); 8.42 (d); 8.67 (m). |
| I-39 | | m.p. 67° C. |
| I-40 | | m.p. 155° C. |

TABLE C-continued active compounds

| No. | Formula | Phys. data |
| --- | --- | --- |
| I-41 | | $^1$H-NMR (CDCl$_3$) δ = 0.90 (m); 1.20 (m); 1.55 (m); 3.80 (broad); 4.27 (m); 7.15-7.45 (m); 7.80 (t); 7.90 (s); 8.42 (d); 8.67 (m). |
| I-42 | | $^1$H-NMR (CDCl$_3$) δ = 0.90 (m); 1.20 (m); 1.50 (m); 3.67 (broad); 3.77 (m); 7.15-7.45 (m); 7.75 (s); 7.82 (t); 8.42 (d); 8.67 (m). |
| I-43 | | m.p. 152° C. |
| I-44 | | m.p. 112° C. |
| I-45 | | m.p. 131° C. |

TABLE C-continued active compounds

| No. | Formula | Phys. data |
|---|---|---|
| I-46 | | ¹H-NMR (CDCl₃) δ = 1.22 (t); 2.67 (s); 3.63 (m); 3.75 (m); 7.15-7.45 (m); 7.70 (t); 7.77 (s); 8.20 (d). |
| I-47 | | ¹H-NMR (CDCl₃) δ = 1.22 (t); 3.90 (d); 4.33 (m); 7.20 (t); 7.40 (m); 7.63 (s); 7.90 (d). |
| I-48 | | m.p. 78° C. |
| I-49 | | m.p. 118° C. |
| I-50 | | m.p. 183° C. |

TABLE C-continued active compounds

| No. | Formula | Phys. data |
|---|---|---|
| I-51 | | m.p. 119° C. |
| I-52 | | m.p. 154° C. |
| I-53 | | m.p. 129° C. |
| I-54 | | m.p. 129° C. |
| I-55 | | $^1$H-NMR (CDCl$_3$) δ = 2.90 (t); 3.77 (m); 3.86 (s); 3.88 (s); 4.13 (m); 6.70 (m); 7.10 (t); 7.35 (m); 7.80 (t); 7.90 (s); 8.47 (d); 8.73 (m). |

TABLE C-continued

| active compounds | | |
|---|---|---|
| No. | Formula | Phys. data |
| I-56 | | m.p. 78° C. |
| I-57 | | m.p. 59° C. |
| I-58 | | m.p. 201° C. |

Examples of the Action Against Harmful Fungi

The fungicidal action of the compounds of the formula I was demonstrated by the following experiments:

The active compounds were prepared separately as a stock solution with 0.25% by weight of active compound in acetone or DMSO. 1% by weight of the emulsifier Uniperol® EL (wetting agent having emulsifying and dispersing action based on ethoxylated alkylphenols) was added to this solution, and the stock solutions were diluted with water to the desired concentration.

Use Examples

Activity against mildew on cucumber leaves caused by *Sphaerotheca fuliginea* on protective application At the cotyledon stage, leaves of potted cucumber seedlings were sprayed to runoff point with an aqueous suspension having an active compound concentration of 250 ppm. 20 hours after the spray coating had dried on, the plants were inoculated with an aqueous spore suspension of mildew of cucumber (*Sphaerotheca fuliginea*). The plants were then placed in a greenhouse at temperatures between 20 and 24° C. and 60 to 80% relative atmospheric humidity for 7 days. The extent of the mildew development was then determined visually in % infection of the cotyledon area.

In this test, the plants which had been treated with the compounds I-10, I-17, I-30, I-32, I-33, I-42 to I-45, I-51, I-52, I-54 to I-57 or I-58 showed an infection of 15% or less, whereas the untreated plants were 60% infected.

Examples of the Activity Against Animal Pests

The activity of the compounds of the formula I against animal pests was demonstrated by the following tests:
The active compounds were formulated
a) as a 0.1% strength solution in acetone or
b) as a 10% strength emulsion in a mixture of 70% by weight of cyclohexanone, 20% by weight of NekanilR LN (LutensolR AP6, wetting agent having emulsifying and dispersing action based on ethoxylated alkylphenols) and 10% by weight EmulphorR EL (EmulanR EL, emulsifier based on ethoxylated fatty alcohols)

and diluted to the desired concentration, in case a) with acetone and in case b) with water.

In each case the lowest concentration at which the compounds still caused 80-100% inhibition or mortality compared to untreated control experiments (activity threshold or minimum concentration) was determined after the conclusion of the tests.

We claim:
1. A 2-substituted pyridine of the formula I

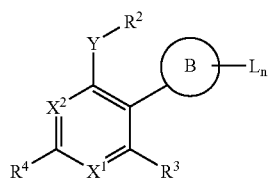

in which the indices and the substituents are as defined below:
$X^1$, $X^2$ in each case, one of the two ring members is N, the other is C—H or C-halogen;
Y is a group —N—$R^1$—;
$R^1$, $R^2$ independently of one another are $C_1$-$C_8$-alkyl, $C_2$-$C_8$-alkenyl, $C_2$-$C_8$-alkynyl, $C_3$-$C_6$-cycloalkyl, $C_3$-$C_6$-halocycloalkyl, where $R^1$ and $R^2$ for their part may be partially or fully halogenated or may carry one to four groups $R^v$:
$R^v$ is cyano, $C_1$-$C_6$-alkyl, $C_3$-$C_6$-cycloalkyl, $C_4$-$C_6$-cycloalkenyl, hydroxyl, $C_1$-$C_6$-alkoxy, $C_2$-$C_8$-alkenyloxy, $C_2$-$C_8$-alkynyloxy, $C_3$-$C_6$-cycloalkyloxy, $C_4$-$C_6$-cycloalkenyloxy, $C_1$-$C_6$-alkylthio, —C(=O)-A, —C(=O)—O-A, —C(=O)—N(A')A, C(A')(=N—OA), N(A')A, N(A')-C(=O)-A, N(A")—C(=O)—N(A')A, S(=O)$_m$-A, S(=O)$_m$—O-A or S(=O)$_m$—N(A')A or phenyl, where the phenyl moiety may carry one to three radicals selected from the group consisting of: halogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_1$-$C_6$-alkoxy, cyano, nitro, —C(=O)-A, —C(=O)—O-A, —C(=O)—N(A')A, C(A')(=N—OA), N(A')A;
$R^1$ may additionally be hydrogen;
$R^1$ and $R^2$ may also, together with the nitrogen or carbon atom to which they are attached, form a saturated five- or six-membered ring which may be interrupted by an ether (—O—), carbonyl (C[=O]—), thio (—S—), sulfoxyl (—S[=O]—) or sulfenyl (—SO$_2$—) group or by a further amino —(—N($R^a$)— group, where $R^a$ is hydrogen or $C_1$-$C_6$-alkyl, and/or may comprise one or more substituents from the group consisting of halogen, $C_1$-$C_6$-alkyl, $C_1$-$C_6$-haloalkyl and oxy-$C_1$-$C_3$-alkyleneoxy;
$R^3$ is halogen, cyano, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy, $C_3$-$C_4$-alkenyloxy, $C_3$-$C_4$-alkynyloxy, $C_1$-$C_6$-alkylthio, di-($C_1$-$C_6$-alkyl)amino or $C_1$-$C_6$-alkylamino, where the alkyl, alkenyl and alkynyl radicals of $R^3$ may be substituted by halogen, cyano, nitro, $C_1$-$C_2$-alkoxy or $C_1$-$C_4$-alkoxycarbonyl;
$R^4$ is a five- or six-membered partially unsaturated or aromatic mono- or bicyclic heterocycle which comprises one to four heteroatoms from the group consisting of O, N and S which for its part may be partially or fully halogenated or may carry one to four groups $R^u$:
$R^u$ is cyano, $C_1$-$C_8$-alkyl, $C_2$-$C_8$-alkenyl, $C_2$-$C_8$-alkynyl, $C_1$-$C_6$-alkoxy, $C_3$-$C_6$-cycloalkyl, $C_2$-$C_8$-alkenyloxy, $C_2$-$C_8$-alkynyloxy, $C_4$-$C_6$-cycloalkenyl, $C_3$-$C_6$-cycloalkyloxy, $C_4$-$C_6$-cycloalkenyloxy, —C(=O)-A, —C(=O)—O-A, —C(=O)—N(A')A, C(A')(=N—OA), N(A')A, N(A')-C(=O)-A, N(A")-C(=O)—N(A')A, S(=O)$_m$-A, S(=O)$_m$—O -A or S(=O)$_m$—N(A')A,
where m, A, A', A" are as defined below;
$R^4$ may furthermore be:
cyano, C(=Z)O$R^a$, C(=Z)N$R^aR^b$, C(=Z)N$R^a$-N$R^zR^b$, C(=Z)$R^a$, C$R^aR^b$-O$R^z$, C$R^aR^b$—N$R^zR^c$, ON(=C$R^aR^b$), O—C(=Z)$R^a$, N$R^aR^{b'}$, N$R^a$(C(=Z)$R^b$), N$R^a$(C(=Z)O$R^b$), N$R^a$(C(=Z)-N$R^zR^b$), N$R^a$(N=C$R^cR^b$), N$R^a$—N$R^zR^b$, N$R^z$—O$R^a$, where
Z is O, S, N$R^a$, NO$R^a$ or N-N$R^zR^c$;
$R^a$, $R^b$, $R^c$ independently of one another are hydrogen, $C_1$-$C_6$-alkyl, $C_2$-$C_6$-alkenyl, $C_2$-$C_6$-alkynyl, $C_3$-$C_6$-cycloalkyl or $C_4$-$C_6$-cycloalkenyl;
$R^{b'}$ has the same meanings as $R^b$, except for hydrogen;
$R^z$ has the same meanings as $R^a$ and may additionally be —CO—$R^a$;
where the aliphatic or alicyclic groups of the radical definitions of $R^a$, $R^b$, $R^c$ or $R^z$ for their part may be partially or fully halogenated or may carry one to four groups $R^w$:
$R^w$ is halogen, cyano, $C_1$-$C_8$-alkyl, $C_2$-$C_{10}$-alkenyl, $C_2$-$C_{10}$-alkynyl, $C_1$-$C_6$-alkoxy, $C_2$-$C_{10}$-alkenyloxy, $C_2$-$C_{10}$-alkynyloxy, $C_3$-$C_6$-cycloalkyl, $C_3$-$C_6$-cycloalkenyl, $C_3$-$C_6$-cycloalkoxy, $C_3$-$C_6$-cycloalkenyloxy, and where two of the radicals $R^a$, $R^b$, $R^c$ or $R^z$ together with the atoms, to which they are attached, may form a five- or six-membered saturated, partially unsaturated or aromatic heterocycle which comprises one to four heteroatoms from the group consisting of O, N and S;

is a five- or six-membered hetaryl which comprises 1 to 3 heteroatoms selected from the group consisting of O, N and S or is phenyl;
n is an integer from 1 to 5;
L is halogen, cyano, cyanato (OCN), $C_1$-$C_8$-alkyl, $C_2$-$C_8$-alkenyl, $C_2$-$C_8$-alkynyl, $C_1$-$C_6$-alkoxy, $C_2$-$C_8$-alkenyloxy, $C_2$-$C_8$-alkynyloxy, $C_3$-$C_6$-cycloalkyl, $C_4$-$C_6$-cycloalkenyl, $C_3$-$C_6$-cycloalkyloxy, $C_4$-$C_6$-cycloalkenyloxy, nitro, —C(=O)-A, —C(=O)—O-A, —C(=O)—N(A')A, —C(=S)—N(A')A, C(A')(=N—OA), N(A')A, N(A')-C(=O)-A, N(A")-C(=O)—N(A')A, S(=O)$_m$-A, S(=O)$_m$—O-A or S(=O)$_m$—N(A')A,
m is 0, 1 or 2;

A, A', A" independently of one another are hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, phenyl, where the organic radicals may be partially or fully halogenated or may be substituted by nitro, cyanato, cyano or $C_1$-$C_4$-alkoxy; or A and A' together with the atoms to which they are attached are a five- or six-membered saturated, partially unsaturated or aromatic heterocycle which comprises one to four heteroatoms from the group consisting of O, N and S;

where the aliphatic groups of the radical definitions of L for their part may be partially or fully halogenated or may carry one to four groups $R^L$:

$R^L$ is cyano, $C_1$-$C_6$-alkoxy, $C_3$-$C_6$-cycloalkyl, $C_2$-$C_8$-alkenyloxy, $C_2$-$C_8$-alkynyloxy, $C_4$-$C_6$-cycloalkenyl, $C_3$-$C_6$-cycloalkyloxy, $C_4$-$C_6$-cycloalkenyloxy, —C(=O)-A, —C(=O)—O-A, —C(=O)—N(A')A, C(A')(=N—OA), N(A')A, N(A')—C(=O)-A, N(A")—C(=O)—N(A')A, S(=O)$_m$-A, S(=O)$_m$—O-A or S(=O)$_m$—N(A')A.

2. The 2-substituted pyridine according to claim 1, in which B=phenyl and which corresponds to the formula I':

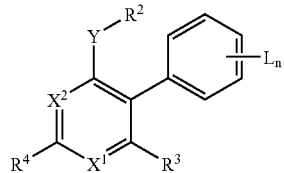

where
Y is a group —N—$R^1$—;
$R^1$, $R^2$ independently of one another are $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl or $C_2$-$C_6$-haloalkynyl;
$R^1$ may additionally be hydrogen;
$R^1$ and $R^2$ may also, together with the nitrogen atom to which they are attached, form a saturated five- or six-membered ring which may be interrupted by an ether (—O—) or by a further amino —(—N($R^a$)—)—group, where $R^a$ is hydrogen or $C_1$-$C_6$-alkyl, and/or may comprise one or more substituents from the group consisting of halogen, $C_1$-$C_6$-alkyl, $C_1$-$C_6$-haloalkyl and oxy-$C_1$-$C_3$-alkyleneoxy;
$R^3$ is halogen, cyano, $C_1$-$C_4$-alkyl, $C_1$-$C_4$-alkoxy or $C_1$-$C_4$-haloalkyl;
$R^4$ is pyrrole, pyrazole, imidazole, 1,2,3-triazole, 1,2,4-triazole, tetrazole, oxazole, isoxazole, 1,3,4-oxadiazole, furan, thiophene, thiazole, isothiazole, pyridine, pyrimidine, pyrazine, pyridazine, 1,2,3-triazine, 1,2, 4-triazine, or 1-pyridin( 1,2,-dihydro) -2-one, where the heterocycle may be attached via C or N to the pyrimidine ring and may carry up to three substituents $R^u$.
$R^u$ is halogen, cyano, $C_1$-$C_8$-alkyl, $C_1$-$C_6$-alkoxy, —C(=O)-A, —C(=O)—O-A, —C(=O)—N(A')A, C(A')(=N—OA), N(A')A, N(A')—C(=O)-A, or
cyano, C(=O)NR$^z$R$^b$, C(=NOR$^a$)NR$^z$R$^b$, C(=NOR$^b$)R$^a$, C(=N—NR$^z$R$^b$)R$^a$ or CR$^a$R$^b$—NR$^z$R$^c$, ON(=CR$^a$R$^b$), NR$^a$(C(=O)R$^b$), NR$^a$(C(=O)OR$^b$), NR$^a$(N=CR$^c$R$^b$) or NR$^z$—OR$^a$.

n is an integer from 1 to 3 where at least one substituent L is located in the ortho-position on the phenyl ring;
L is halogen, cyano, methyl, methoxy, —C(=O)—O-A, —C(=O)—N(A')A, —C(=S)—N(A')A, C(A')(=N—OA), N(A')A, N(A')—C(=O)-A,
A,A' independently of one another are hydrogen, $C_1$-$C_6$-alkyl, $C_2$-$C_6$-alkenyl, $C_2$-$C_6$-alkynyl, phenyl, where the organic radicals may be partially or fully halogenated or may be substituted by $C_1$-$C_4$-alkoxy; or A and A'together with the atoms to which they are attached are a five- or six-membered saturated heterocycle which comprises one or two heteroatoms from the group consisting of O, N and S;
where the aliphatic groups of the radical definitions of L for their part may be partially or fully halogenated.

3. The 2-substituted pyridine according to claim 1 in which $R^4$ is 1-pyrazole, 1-[1,2,4] triazole, 2-pyridine, 2-pyrimidine, 3-pyridazine, or 1-pyridin(1,2,-dihydro)-2-one.

4. The 2-substituted pyridine according to claim 1 in which $R^4$ is C(=Z)OR$^a$, C(=Z)NR$^z$R$^b$ or C(=Z)R$^a$ and
Z is O, NR$^a$ or NOR$^a$.

5. The 2-substituted pyridine according to claim 1 in which
Y is a group —N—$R^1$—, where $R^1$ hydrogen and p1 $R^2$ is $C_3$-$C_8$-alkyl, $C_3$-$C_8$-alkenyl, $C_3$-$C_8$-alkynyl or $C_3$-$C_6$-haloalkyl branched in the α-position.

6. The 2-substituted pyridine according to claim 1 in which B is $L_n$-substituted phenyl and is represented by

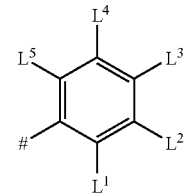

where # is the point of attachment to the pyridine skeleton and
$L^1$ is fluorine, chlorine, $CH_3$ or $CF_3$;
$L^2$, $L^4$ independently of one another are hydrogen, $CH_3$ or fluorine;
$L^3$ is hydrogen, fluorine, chlorine, bromine, nitro, cyano, $CH_3$, $SCH_3$, $OCH_3$, $SO_2CH_3$, CO—$NH_2$, CO—$NHCH_3$, CO—$NHC_2H_5$, CO—$N(CH_3)_2$, CS—$NH_2$, CS—$NHCH_3$, CS—$N(CH_3)_2$, NH—C(=O)$CH_3$, $N(CH_3)$—C(O)$CH_3$ or COOCH$_3$ and
$L^5$ is hydrogen, fluorine, chlorine or $CH_3$.

7. A process for preparing the compounds I* and I**,

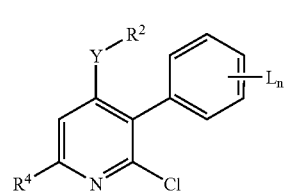

-continued

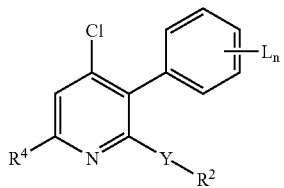

where the substituents Y, $R^2$, $R^4$ and $L_n$ are as defined in claim 2, by reacting phenylacetonitrile II

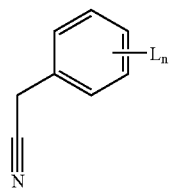

and malonyl chloride to give the dihydroxypyridine III

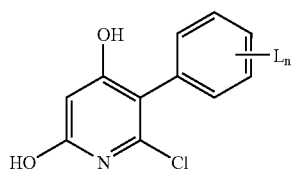

which is reacted with phosphorus oxychloride to give the trichloropyridine IV

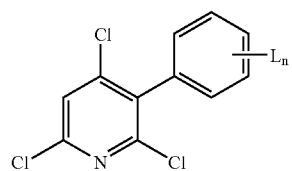

and reacted with $R^4W$, where W is hydrogen or an organometallic radical, to give the intermediate V

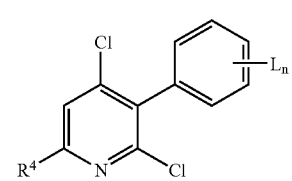

which is finally reacted with $R^2YW'$, where W' is hydrogen or an organometallic radical.

8. A pesticidal composition which comprises a solid or liquid carrier and a compound of the formula I according to claim 1.

9. The 2-substituted pyridine according to claim 2 in which B is $L_n$-substituted phenyl and is represented by

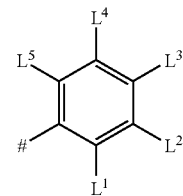

where # is the point of attachment to the pyridine skeleton and $L^1$ is fluorine, chlorine, $CH_3$ or $CF_3$;

$L^2$, $L^4$ independently of one another are hydrogen, $CH_3$ or fluorine;

$L^3$ is hydrogen, fluorine, chlorine, bromine, nitro, cyano, $CH_3$, $SCH_3$, $OCH_3$, $SO_2CH_3$, $CO-NH_2$, $CO-NHCH_3$, $CO-NHC_2H_5$, $CO-N(CH_3)_2$, $CS-NH_2$, $CS-NHCH_3$, $CS-N(CH_3)_2$, $NH-C(=O)CH_3$, $N(CH_3)-C(=O)CH_3$ or $COOCH_3$ and $L^5$ is hydrogen, fluorine, chlorine or $CH_3$.

10. The 2-substituted pyridine according to claim 3 in which B is $L_n$-substituted phenyl and is represented by

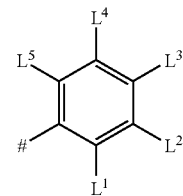

where # is the point of attachment to the pyridine skeleton and $L^1$ is fluorine, chlorine, $CH_3$ or $CF_3$;

$L^2$, $L^4$ independently of one another are hydrogen, $CH_3$ or fluorine;

$L^3$ is hydrogen, fluorine, chlorine, bromine, nitro, cyano, $CH_3$, $SCH_3$, $OCH_3$, $SO_2CH_3$, $CO-NH_2$, $CO-NHCH_3$, $CO-NHC_2H_5$, $CO-N(CH_3)_2$, $CS-NH_2$, $CS-NHCH_3$, $CS-N(CH_3)_2$, $NH-C(=O)CH_3$, $N(CH_3)-C(=O)CH_3$ or $COOCH_3$ and $L^5$ is hydrogen, fluorine, chlorine or $CH_3$.

11. The 2-substituted pyridine according to claim 4 in which B is $L_n$-substituted phenyl and is represented by

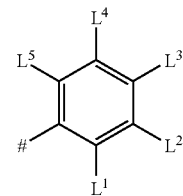

where # is the point of attachment to the pyridine skeleton and $L^1$ is fluorine, chlorine, $CH_3$ or $CF_3$;

$L^2$, $L^4$ independently of one another are hydrogen, $CH_3$ or fluorine;

$L^3$ is hydrogen, fluorine, chlorine, bromine, nitro, cyano, $CH_3$, $SCH_3$, $OCH_3$, $SO_2CH_3$, $CO-NH_2$, $CO-NHCH_3$, $CO-NHC_2H_5$, $CO-N(CH_3)_2$, $CS-NH_2$, $CS-NHCH_3$, $CS-N(CH_3)_2$, $NH-C(=O)CH_3$, $N(CH_3)-C(=O)CH_3$ or $COOCH_3$ and $L^5$ is hydrogen, fluorine, chlorine or $CH_3$.

* * * * *